(12) United States Patent
Bernabe et al.

(10) Patent No.: US 8,013,173 B2
(45) Date of Patent: Sep. 6, 2011

(54) METHOD OF PURIFYING DIANHYDRIDES, THE DIANHYDRIDES FORMED THEREBY, AND POLYETHERIMIDES FORMED THEREFROM

(75) Inventors: Beatriz Penalver Bernabe, Chicago, IL (US); Vijay Gopalakrishnan, Evansville, IN (US); Lioba Maria Kloppenburg, Mount Vernon, IN (US); Matt Kuhlman, Evansville, IN (US); Roy Ray Odle, Mount Vernon, IN (US); Eric Pressman, East Greenbush, NY (US); Narayan Ramesh, Evansville, IN (US); Harpreet Singh, Evansville, IN (US)

(73) Assignee: Sabic Innovative Plastics IP B.V. (NL)

( * ) Notice: Subject to any disclaimer, the term of this patent is extended or adjusted under 35 U.S.C. 154(b) by 21 days.

(21) Appl. No.: 12/058,344

(22) Filed: Mar. 28, 2008

(65) Prior Publication Data
US 2009/0247727 A1    Oct. 1, 2009

(51) Int. Cl.
*C07D 493/00* (2006.01)
(52) U.S. Cl. ......... 549/239; 549/236; 549/241; 549/247
(58) Field of Classification Search .................. 549/236, 549/239, 241, 547, 247
See application file for complete search history.

(56) References Cited

U.S. PATENT DOCUMENTS

| | | | |
|---|---|---|---|
| 4,757,149 A | 7/1988 | Maresca | |
| 4,780,544 A | 10/1988 | Berdahl | |
| 4,808,731 A | 2/1989 | Berdahl et al. | |
| 4,874,835 A | 10/1989 | Berdahl | |
| 4,933,469 A | 6/1990 | Berdahl et al. | |
| 5,021,168 A | 6/1991 | Molinaro et al. | |
| 6,028,203 A | 2/2000 | Brunelle et al. | |
| 6,204,394 B1 | 3/2001 | Sakata et al. | |
| 6,706,897 B1 | 3/2004 | Brunelle et al. | |
| 6,727,370 B1 | 4/2004 | Brunelle et al. | |
| 7,495,113 B2 * | 2/2009 | Pressman et al. | 549/239 |
| 2006/0135791 A1 * | 6/2006 | Pressman et al. | 549/281 |
| 2006/0293528 A1 * | 12/2006 | Stella et al. | 549/243 |
| 2007/0073035 A1 | 3/2007 | Stella et al. | |
| 2007/0073063 A1 | 3/2007 | Stella et al. | |
| 2007/0073066 A1 | 3/2007 | Stella et al. | |
| 2007/0117990 A1 | 5/2007 | Pressman et al. | |

FOREIGN PATENT DOCUMENTS

| | | |
|---|---|---|
| CN | 1324794 | 12/2001 |
| CN | 1370775 | 9/2002 |
| CN | 1706846 | 12/2005 |
| CN | 1827611 | 9/2006 |
| EP | 1674443 A1 | 6/2006 |
| JP | 11158168 | 6/1999 |
| JP | 2005145838 | 6/2005 |
| JP | 2005350434 | 12/2005 |
| JP | 2006188502 | 7/2006 |
| JP | 2006213646 | 8/2006 |
| WO | W09827047 A1 | 6/1998 |

OTHER PUBLICATIONS

European Patent Office, PCT International Search Report, International Application No. PCT/US2008/058678, Date of Mailing: Dec. 12, 2008.
European Patent Office, PCT Written Opinion of the ISA, International Application No. PCT/US2008/058678, Date of Mailing: Dec. 12, 2008.
Wu et al., "Synthesis technology of tetracarboxylic dianhydride monomers for polyimide," (Abstract) Journal Huaxue Yu Nianhe (2002, (4), 173-175, School of Chemistry and Chemical Engineering, Heilongjiang University, Harbin, 150080, Peop. Rep. China.

* cited by examiner

*Primary Examiner* — James Seidleck
*Assistant Examiner* — Gregory Listvoyb
(74) *Attorney, Agent, or Firm* — Cantor Colburn LLP; Diderico van Eyl

(57) ABSTRACT

A method for purifying an oxydiphthalic anhydride comprises diluting a first mixture comprising an oxydiphthalic anhydride, a solvent, a catalyst, and an inorganic salt with a solvent, to provide a second mixture having a solids content of 10 to 30 percent based on total weight of the second mixture; filtering and washing the solids of the second mixture at a temperature below the crystallization point temperature of the oxydiphthalic anhydride to provide a third mixture; hydrolyzing the third mixture by adding water and a water-soluble acid to form a fourth mixture; heating the fourth mixture; then cooling to provide a solid-liquid mixture, optionally decanting a portion of the liquid, rediluting the remaining solid-liquid mixture, then filtering to provide a solid component; washing the solid component with water to provide a fifth mixture of oxydiphthalic tetraacid and water; ring closing the oxydiphthalic tetraacid to provide oxydiphthalic anhydride, and filtering the oxydiphthalic anhydride.

28 Claims, 6 Drawing Sheets

METHOD OF PURIFYING DIANHYDRIDES, THE DIANHYDRIDES FORMED THEREBY, AND POLYETHERIMIDES FORMED THEREFROM

BACKGROUND OF THE INVENTION

This invention relates to a method for purifying a dianhydride, the dianhydrides formed thereby, and polyetherimides formed therefrom. More particularly, the method relates to purifying an oxydiphthalic anhydride.

Oxydiphthalic anhydride, a monomer prized as a component of a unique class of high temperature polyetherimides, may be prepared from chlorophthalic anhydride by coupling two molecules of chlorophthalic anhydride in the presence of an inorganic carbonate, a solvent and a phase transfer catalyst. The crude product of such a coupling reaction often includes the solvent, unreacted starting material(s), phase transfer catalyst, inorganic by-products, and other impurities, which must be separated from the oxydiphthalic anhydride prior to its use in polymer synthesis.

The purification of anhydrides generally has been the focus of an extensive research effort. For example, various processes have been advanced for the purification of phthalic anhydride and pyromellitic acid using activated carbon and are disclosed in U.S. Pat. Nos. 1,301,388; 2,937,189; 2,985,665; 3,236,885; and 3,236,885. U.S. Pat. No. 2,786,805 teaches that phthalic anhydride can be purified by making a slurry of the material in water, heating the slurry to 375° F. to 400° F. (191° C. to 204° C.), removing the anhydride by passing steam into the mixture and condensing the purified phthalic anhydride vapors. U.S. Pat. No. 3,338,923 discloses a method of purifying pyromellitic dianhydride by treatment with ketones. Furthermore, U.S. Pat. No. 3,338,923 discloses that the material can be purified by converting the dianhydride into the corresponding acid with water and recrystallizing the acid from water in the presence of activated carbon.

U.S. Pat. No. 4,906,760 discloses the removal of various metal ion impurities from aromatic anhydrides. U.S. Pat. No. 4,906,760 likewise discloses the removal of metal ion impurities from aromatic anhydrides.

U.S. Pat. No. 4,870,194 discloses a purification scheme for oxydiphthalic anhydride. U.S. Pat. No. 5,145,971 likewise discloses a process for the preparation of purified oxydiphthalic acid from impure oxydiphthalic anhydride. U.S. Pat. No. 5,336,788 discloses the conversion of oxydiphthalic acid to oxydiphthalic anhydride Previous research efforts and achievements notwithstanding, there is a continuing need to develop improved processes for the purification of oxydiphthalic anhydrides. Purification of oxydiphthalic anhydrides is challenging, in part, because certain materials used in methods are soluble in organic solvents while other components are substantially insoluble in the organic solvents. The disparate solubility properties of the materials make it difficult to create a single process that addresses such different solubility properties. The disparate solubility properties of the materials also make it difficult to obtain a high purity/high quality oxydiphthalic anhydride. Further, purification of oxydiphthalic anhydrides is challenging, in part, because manufacturing conditions require processes to produce high purity/high quality oxydipthalic anhydrides economically with minimal use of solvent.

For the foregoing reasons, there is a need to develop methods for purifying dianhydrides, and in particular oxydiphthalic anhydrides, that consume the least solvent without degrading yield or purity.

BRIEF SUMMARY OF THE INVENTION

In one embodiment a method for purifying an oxydiphthalic anhydride having structure (I), comprises steps (a) to (f),

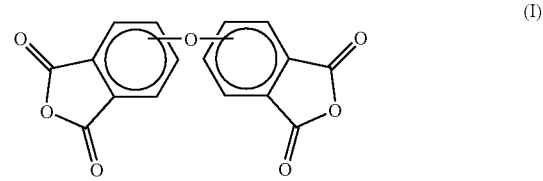

(I)

(a) providing a first mixture comprising at least one oxydiphthalic anhydride, at least one solvent, at least one catalyst, and at least one inorganic salt selected from the group consisting of alkali metal halide salts, alkaline earth metal halide salts, and mixtures thereof, the oxydiphthalic anhydride being present in the first mixture in an amount of 10 to 30 percent by weight based on total weight of the first mixture;
(b) diluting the first mixture with at least one solvent, to provide a second mixture having a solids content of 10 to 30 percent based on total weight of the second mixture;
(c) filtering the second mixture at a temperature below the crystallization point temperature of the oxydiphthalic anhydride and washing the solid with solvent to provide a mother liquor, a wash liquor, and a third mixture of the oxydiphthalic anhydride and salts;
(d) hydrolyzing by adding (1) a water-soluble acid having a $pK_a$ less than or equal to the $pK_a$ of oxydiphthalic tetraacid and (2) water to the third mixture, forming a fourth mixture, and heating the fourth mixture; wherein the fourth mixture is cooled to provide a solid-liquid mixture; filtering the solid-liquid mixture to provide a mother liquor and solid component; and washing the solid component is washed with water to provide wash liquor and a fifth mixture of oxydiphthalic tetraacid and water; and
(e) ring closing the oxydiphthalic tetraacid by heating the fifth mixture under a temperature and pressure sufficient to convert the oxydiphthalic tetraacid to the oxydiphthalic anhydride, forming a sixth mixture; and
(f) filtering the sixth mixture to obtain substantially pure oxydiphthalic anhydride.

In one embodiment is disclosed an oxydiphthalic anhydride purified by the above-described method, wherein the sixth mixture from step (e) comprises less than 50 ppm (parts per million) alkali metal ion, less than 1000 ppm chlorophthalic anhydride, and less than 30 ppm catalyst, based on total weight of the oxydiphthalic anhydride in the sixth mixture; and the at least one solvent of step (b) is recycled mother liquor and wash liquor from step (c) obtained from a previous batch of first mixture.

In another embodiment is disclosed a polyetherimide derived from an oxydiphthalic anhydride purified by the above-described method, wherein the sixth mixture from step (f) comprises less than 50 ppm alkali metal ion, less than 1000 ppm chlorophthalic anhydride, and less than 30 ppm catalyst, based on total weight of the oxydiphthalic anhydride present in the sixth mixture, and the at least one solvent of step (b) is recycled mother liquor and wash liquor from step (c) obtained from a previous batch of first mixture.

In one embodiment, a method for purifying 4,4'-oxydiphthalic anhydride having structure (II) comprises steps (a) through (f):

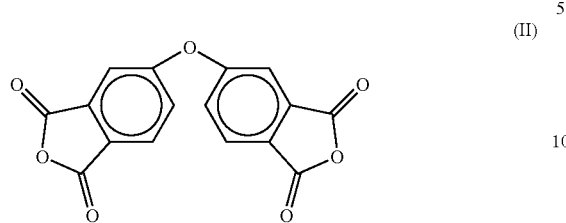

(II)

(a) providing a first mixture comprising 4,4'-oxydiphthalic anhydride, ortho-dichlorobenzene, at least one catalyst including hexaethylguanidinium chloride, and potassium chloride, the 4,4'-oxydiphthalic anhydride being present in the first mixture in an amount of 10 to 30 percent by weight based on total weight of the first mixture;

(b) diluting the first mixture with ortho-dichlorobenzene to provide a second mixture having a solids content of 10 to 30 percent based on total weight of the second mixture;

(c) filtering the second mixture at a temperature of 5° C. to 150° C. and washing the solid with ortho-dichlorobenzene to provide a mother liquor, a wash liquor, and a third mixture of the 4,4'-oxydiphthalic anhydride and potassium chloride;

(d) hydrolyzing by adding phosphoric acid and water to the third mixture, then filtering, forming a fourth mixture and heating the fourth mixture and subsequently cooling the fourth mixture, wherein a portion of the liquid of the fourth mixture is decanted, rediluted with water, filtered and washed with water to provide wash liquor and a fifth mixture of 4,4'-oxydiphthalic tetraacid and water;

(e) ring closing the 4,4'-oxydiphthalic tetraacid by heating the fifth mixture under a temperature and pressure sufficient to convert the 4,4'-oxydiphthalic tetraacid to the 4,4'-oxydiphthalic anhydride, forming a sixth mixture; and (f) filtering the sixth mixture to obtain substantially pure 4,4'-oxydiphthalic anhydride.

DETAILED DESCRIPTION OF THE INVENTION

Figure 1:
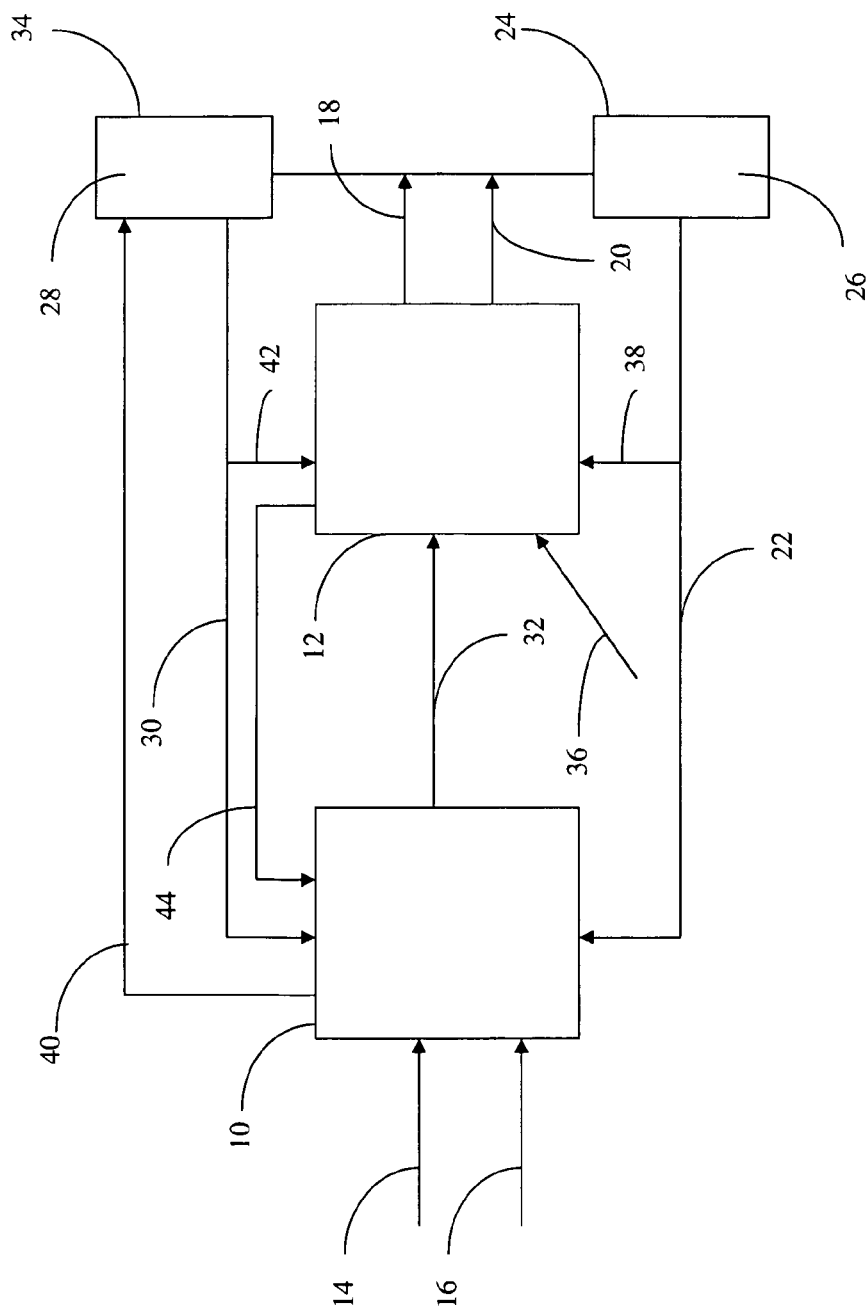
FIG. 1 is a schematic showing how solvent is recycled in the disclosed method of purifying oxydiphthalic anhydride.

The invention is based oil the discovery that by practicing a specific combination of dilution, filtering, hydrolysis, ring closing, and filtering steps, it is possible to purify an oxydiphthalic anhydride in a process that produces certain materials that are both soluble and insoluble in organic solvents and obtain a high purity and high quality oxydiphthalic anhydride product in a single process. The invention is also based on the discovery that by practicing such a sequence of steps with a reused/recycled organic solvent and reused/recycled water (materials that contain a high level of impurities and that are ordinarily discarded in processes), it is possible to purify an oxydiphthalic anhydride under certain conditions and obtain a product of high purity and quality. Advantageously, the process minimizes solvent usage, reduces costs for manufactures, and reduces waste streams produced by a manufacturing plant. The present method of purifying an oxydiphthalic anhydride may be understood more readily by reference to the following detailed description of preferred embodiments and the examples included therein. In the following specification and the claims which follow, reference will be made to a number of terms which shall be defined to have the following meanings:

The singular forms "a", "an" and "the" include plural references unless the context clearly dictates otherwise. The endpoints of all ranges directed to the same characteristic or component are independently combinable and inclusive of the recited endpoint.

"Optional" or "optionally" means that the subsequently described event or circumstance may or may not occur, and that the description includes instances where the event occurs and instances where it does not.

As used herein, the phrase "dissolving substantially all of the oxydiphthalic anhydride present" means dissolving at least 90 percent of the oxydiphthalic anhydride present.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical may also include non-aromatic components. For example, a benzyl group is an aromatic radical which comprises a phenyl ring (the aromatic group) and a methylene group (the non-aromatic component). Similarly a tetrahydronaphthyl radical is an aromatic radical comprising an aromatic group ($C_6H_3$) fused to a non-aromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3-$CCl_3$Ph-), 4-(3-bromoprop-1-yl)phen-1-yl (i.e. 4-BrCH$_2$CH$_2$CH$_2$Ph-), and the like. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g., methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more non-cyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the non-cyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (e.g. carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexa fluoroisopropylidene-2,2-bis(cyclohex-4-yl) (i.e., —$C_6H_{10}$C($CF_3$)$_2$$C_6H_{10}$—), 2-chloromethylcyclolex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3$CHBrCH$_2$$C_6H_{10}$—), and the like. Further examples of cycloaliphatic radicals include 4-allyloxycyclohex-1-yl, 4-aminocyclohex-1-yl (i.e., $H_2$$C_6H_{10}$—), 4-aminocarbonylcyclopent-1-yl (i.e., NH$_2$COC$_5H_8$—), 4-acetyloxycyclohex-1-yl, 2,2-dicyanoisopropylidenebis(cyclohex-4-yloxy) (i.e., —OC$_6H_{10}$C(CN)$_2$C$_6H_{10}$O—), 3-methylcyclohex-1-yl, methylenebis(cyclohex-4-yloxy) (i.e., —OC$_6H_{10}$CH$_2$C$_6H_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6H_{10}$(CH$_2$)$_6$C$_6H_{10}$O—), 4-hydroxymethylcyclohex-1-yl (i.e., 4-HOCH$_2$C$_6H_{10}$—), 4-mercaptomethylcyclohex-1-yl (i.e., 4-HSCH$_2$C$_6H_{10}$—), 4-methylthiocyclohex-1-yl (i.e., 4-CH$_3$SC$_6H_{10}$—), 4-methoxycyclohex-1-yl, 2-methoxycarbonylcyclohex-1-yloxy (2-CH$_3$OCOC$_6H_{10}$O—), 4-nitromethylcyclohex-1-yl (i.e., NO$_2$CH$_2$C$_6H_{10}$—), 3-trimethylsilylcyclohex-1-yl, 2-t-butyldimethylsilylcyclopent-1-yl, 4-trimethoxysilylethylcyclohex-1-yl (e.g., (CH$_3$O)$_3$SiCH$_2$CH$_2$C$_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a $C_4$ cycloaliphatic radical. The cyclohexylmethyl radical (C$_6$H$_{11}$CH$_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example, carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e. —CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e., CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e. (CH$_3$)$_3$Si—), t-butyldimethylsilyl, 3-trimethyoxysilypropyl (i.e., (CH$_3$O)$_3$SiCH$_2$CH$_2$—), vinyl, vinylidene, and the like. By way of further example, a $C_1$-$C_{10}$ aliphatic radical contains at least one but no more than 10 carbon atoms. A methyl group (i.e., CH$_3$—) is an example of a C$_1$ aliphatic radical. A decyl group (i.e., CH$_3$(C$_2$)$_9$—) is an example of a C$_{10}$ aliphatic radical.

As noted, in a first aspect, the present invention relates to a method for purifying an oxydiphthalic anhydride having structure (I), the method comprising steps (a) to (f),

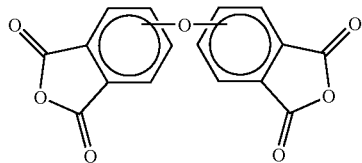

(a) providing a first mixture comprising at least one oxydiphthalic anhydride, at least one solvent, at least one catalyst, and at least one inorganic salt selected from the group consisting of alkali metal halide salts, alkaline earth metal halide salts, and mixtures thereof, the oxydiphthalic anhydride being present in the first mixture in an amount of 10 to 30 percent by weight based on total weight of the first mixture;

(b) diluting the first mixture with at least one solvent, to provide a second mixture having a solids content of 10 to 30 percent based on total weight of the second mixture;

(c) filtering the second mixture at a temperature below the crystallization point temperature of the oxydiphthalic anhydride and washing the solid with solvent to provide a mother liquor, a wash liquor, and a third mixture of the oxydiphthalic anhydride and salts;

(d) hydrolyzing the third mixture by adding (1) a water-soluble acid having a pK$_a$ less than or equal to the pK$_a$ of oxydiphthalic tetraacid and (2) water to form a fourth mixture and heating the fourth mixture, followed by cooling the fourth mixture to provide a solid-liquid mixture; optionally decanting a portion of the liquid then rediluting the remaining solid-liquid mixture with water; then filtering the solid-liquid mixture or rediluted solid-liquid mixture to provide a mother liquor and solid component; and washing the solid component with water to provide a wash liquor and a fifth mixture comprising oxydiphthalic tetraacid and water;

(e) ring closing the oxydiphthalic tetraacid by heating the fifth mixture under a temperature and pressure sufficient to convert the oxydiphthalic tetraacid to the oxydiphthalic anhydride, forming a sixth mixture; and (f) filtering the sixth mixture to obtain substantially pure oxydiphthalic anhydride.

In one embodiment, the catalyst of the first mixture is selected from the group consisting of hexaethylguanidinium chloride, hexaethylguanidinium bromide, hexa-n-butylguanidinium bromide, 1,6-bis(N,N',N',N'',N''-penta-n-butylguanidinium)hexane dibromides, 1,6-bis(N-n-butyl-N',N',N'',N''-tetraethylguanidinium)hexane dibromides, phosphonium salts, and combinations thereof.

The disclosed method employs non-recycled and recycled organic solvent. The mother liquor and the wash liquor of step (c) can also be referred to as the first mother liquor and the first wash liquor, respectively. The mother liquor and wash liquor of step (d) can also be referred to as the second mother liquor and the second wash liquor, respectively. In filtering the sixth mixture, additional mother liquor and wash liquor are obtained, also referred to as third mother liquor and third wash liquor respectively. Each of the above named first, second and third mother liquors, and first, second, and third wash liquors are potentially recyclable. In one embodiment, the solvent of step (b) is recycled mother liquor or wash liquor or mixtures thereof from step (c) obtained from a previous batch of first mixture. In another embodiment, the mother liquor, wash liquor, or mixtures thereof are recycled for a sufficient number of times to achieve a steady state concentration of impurities, including at least one of chlorophthalic anhydride, catalyst, hydroxyphthalic anhydride, and oxydiphthalic anhydride in the mother liquor or wash liquor. In one embodiment the mother liquor or wash liquor or mixtures thereof, are recycled 1 to 20,000 times.

The disclosed method also employs non-recycled and recycled aqueous solvents. In one embodiment, the water of step (d) is recycled water from a component selected from the group consisting of mother liquor, wash liquor, and combinations thereof, from step (d) obtained from a previous batch of fifth mixture. In another embodiment, the water wash liquor from step (d) is recycled one or more times. In still another embodiment, the water wash liquor from step (d) is recycled from one to 20,000 times.

Recycled solvent usage is schematically represented in FIG. 1, and applies to both organic and aqueous solvents. Reaction slurry 14 is First introduced into feed tank 10, where the mother liquor can optionally be decanted. In those instances when decanting is desired, the decanted mother liquor is fed via pathway 40 to mother liquor tank 34 for recycling. Slurry 14 is diluted with at least fresh solvent 16 and/or recycled solvent including recycled wash liquor 26 and/or recycled mother liquor 28 obtained from a previous batch of the slurry. Recycled wash liquor 26 is directed into feed tank 10 from wash liquor tank 24 via pathway 22. Wash liquor tank 24 is also referred to as a blow down tank for receiving holdup solvent from filtration unit 12. Recycled mother liquor 28 is directed into feed tank 10 via pathway 30 from mother liquor tank 34. The diluted slurry in feed tank 10 is then directed to a filtration unit 12 via pathway 32. The slurry can be cycled between the filtration unit 12 and feed tank 10 by pathways 44 and 32 to effect desired conditioning of the filtration unit when desired. The slurry is then filtered to produce a wet cake and mother liquor. The mother liquor is directed to mother liquor tank 34 for recycling via pathway 18. The wet cake is washed with fresh solvent delivered via pathway 36 and/or optionally recycled solvent, including wash liquor 26 introduced via pathway 38 and/or recycled mother liquor 28 introduced via pathway 42. In one embodiment, the mother liquor 28 and wash liquor 26 are recycled individually. In one embodiment the mother liquor 28 and wash liquor 26 are combined and recycled together. This solvent recycling scheme is applicable to each of the dilution, decanting and filtering steps.

Low impurity levels are obtained in various steps of the purification method. In one embodiment, the third mixture of step (c) comprises less than 2 weight percent chlorophthalic anhydride. In one embodiment, the third mixture also comprises less than 2 weight percent of a catalyst. In one embodiment, the fifth mixture of step (d) comprises less than 200 ppm of a catalyst. In one embodiment, the fifth mixture of step (d) comprises less than 30 ppm of a catalyst. In one embodiment, the sixth mixture of step (f) comprises less than 100 ppm of an alkali metal ion or alkaline earth metal ion based on the weight of the oxydiphthalic anhydride present in the sixth mixture. In another embodiment, the sixth mixture comprises less than 2000 ppm chlorophthalic acid based on the weight of the oxydiphthalic anhydride present in the sixth mixture. In yet another embodiment, the sixth mixture of step (e) contains phosphorous in an amount that is less than 100 ppm based on the weight of the oxydiphthalic anhydride present in the sixth mixture.

The oxydiphthalic anhydrides represented by generic structure (I) are hereinafter sometimes referred to as "ODPA". The oxydiphthalic anhydrides represented by structure (I) may also be referred to as "bisanhydrides." The genus represented by structure (I) includes within it pure oxydiphthalic anhydrides such as 4,4'-oxydiphthalic anhydride, 3,3'-oxydiphthalic anhydride, and 3,4'-oxydiphthalic anhydride. Alternately, the genus represented by structure (I) includes mixtures of oxydiphthalic anhydrides, for example a mixture of 4,4'-oxydiphthalic anhydride and 3,3'-oxydiphthalic anhydride. In one embodiment, structure (I) represents a bisanhydride consisting essentially of 3,3'-oxydiphthalic anhydride. In an alternate embodiment, structure (I) represents a bisanhydride consisting essentially of 3,4'-oxydiphthalic anhydride. In yet another embodiment, structure (I) represents a mixture of 3,3'-oxydiphthalic anhydride and 3,4'-oxydiphthalic anhydride. In alternate embodiments, minor amounts (i.e., each of the "minor" components represents less than about 5 percent by weight of the total weight of the composition) of the 3,3'-oxydiphthalic anhydride and 3,4'-oxydiphthalic anhydride are present in an oxydiphthalic anhydride consisting primarily of 4,4'-oxydiphthalic anhydride. The term "consisting primarily of" refers to a composition having a major component which represents 90 percent by weight or more of the total weight of the composition. In one embodiment the oxydiphthalic anhydride comprises 4,4'-oxydiphthalic anhydride having structure (II).

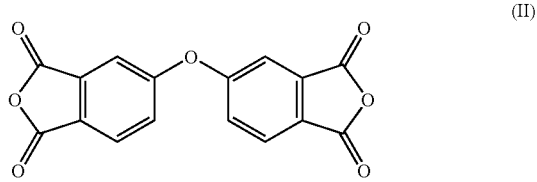

(II)

As noted, the method for the purification of an oxydiphthalic anhydride comprises steps (a) to (f) in which a first mixture of step (a) comprises at least one oxydiphthalic anhydride, at least one solvent and at least one inorganic salt. Thereafter, the additional steps (diluting the first mixture with a solvent to provide a second mixture (step (b)), filtering the oxydiphthalic anhydride present in the second mixture to provide a third mixture (step (c)), hydrolyzing by adding acid and water to form a fourth mixture, and heating the fourth mixture to provide a fifth mixture comprising oxydiphthalic tetraacid and water (step (d)), ring closing the oxydiphthalic tetraacid by heating the fifth mixture to form a sixth mixture of the oxydiphthalic anhydride (step (e)), and filtering the sixth mixture (step (f))), provide the purified oxydiphthalic anhydride. In each of the steps (a) to (d), the presence of at least one solvent is required. Step (e), heating the fifth mixture, can be carried out with or without the presence of organic solvent, but more particularly with an organic solvent.

Exemplary solvents include non-polar solvents and polar aprotic solvents. Typically, the first mixture (step (a)) comprises an aromatic solvent, for example an aromatic hydrocarbon solvent or chloroaromatic solvent. In one embodiment the solvent has a boiling point above about 120° C., preferably above about 150° C. and more preferably above about 180° C. In one embodiment, the solvent is selected from the group consisting of chlorobenzene, ortho-dichlorobenzene (o-dichlorobenzene or oDCB), para-dichlorobenzene, 2,4-dichlorotoluene, 1,2,4-trichlorobenzene, diphenyl sulfone, phenetole, anisole, veratrole, toluene, xylene, mesitylene and mixtures thereof. In one embodiment one or more chlorinated aromatic solvents are employed. Exemplary chlorinated aromatic solvents include, but are not limited to chlorobenzene, ortho-dichlorobenzene, 2,4-dichlorotoluene, and 1,2,4-trichlorobenzene. In one embodiment 2,4-dichlorotoluene is employed. In an alternate embodiment at least one solvent of step (a) is ortho-dichlorobenzene. The use of a relatively high boiling solvent, such as the aromatic solvents exemplified here, allows for example, the heating step (e) to be carried out at temperatures which exceed the boiling point of the solvent at relatively modest super-atmospheric pressures, and correspondingly higher rates of dissolution. In one embodiment, water and organic solvents are used in step (d). In certain embodiments it is found expedient to remove a portion of the solvent in order to for example, further dry or concentrate the oxydiphthalic anhydride containing mixture or solution. Certain solvents provide for azeotropic distillation of water present in the mixture. Examples of solvents which form azeotropes with water, include but are not limited to, toluene and ortho-dichlorobenzene. In one embodiment solvent is distilled from the fifth mixture at super-atmospheric pressure in order to remove water. In yet another embodiment, solvent is distilled from the homogeneous solution of the oxydiphthalic anhydride formed in step (e). The ODPA needs to be in solution to filter effectively. In general, solvent removal by distillation may be carried out at any point during the process and may be conducted at atmospheric pressure, sub-atmospheric pressure, or super-atmospheric pressure.

As noted, the first mixture comprises at least one inorganic salt contaminant. The origin of the inorganic salt is not limited to a particular source. The at least one inorganic salt may be present as the by-product of the reaction used to form the oxydiphthalic anhydride, or the inorganic salt may be present as a contaminant from another source, for example the adventitious contamination of an oxydiphthalic anhydride by potassium chloride during handling. Typically, however, the inorganic salt is the by-product of the reaction used to prepare the oxydiphthalic anhydride itself. For example, the potassium chloride formed as a by-product in the reaction of potassium carbonate with 4-chlorophthalic anhydride in ortho-dichlorobenzene at elevated temperature (for example, 180° C.) in the presence of an organic catalyst such as hexaethylguanidinium chloride, the product of this reaction being a first mixture comprising ortho-dichlorobenzene solvent, solid oxydiphthalic anhydride, solid potassium chloride, and the catalyst hexaethylguanidinium chloride. Typically, the at least one inorganic salt is an alkali metal halide, an alkaline earth metal halide, or a mixture thereof. With respect to alkali metal halides and alkaline earth metal halides, the term "mixtures thereof" includes mixtures of two or more alkali metal halides, mixtures of two or more alkaline earth metal halides, and mixtures of at least one alkali metal halide with at least one alkaline earth metal halide. Alkali metal halides are illustrated by sodium chloride, potassium chloride, potassium bromide, potassium fluoride, lithium bromide, cesium chloride, and lithium fluoride. Alkaline earth metal halides are illustrated by magnesium chloride, calcium chloride, calcium bromide, and barium chloride. In a one embodiment, the inorganic salt present as a contaminant in the first mixture is potassium chloride.

In one embodiment of the present invention, the first mixture and the second mixture are substantially anhydrous, the term "substantially anhydrous" denoting a total water content of less than about 50 parts per million (ppm). In an alternate embodiment of the present invention the first mixture is not substantially anhydrous (i.e., has a water content of more than 50 ppm, for example 500 ppm).

In step (a), the oxydiphthalic anhydride is present in the first mixture in an amount corresponding to 10 to 30 weight percent (wt %) based on total weight of the first mixture. In another embodiment, the oxydiphthalic anhydride is present in the first mixture in an amount corresponding to at least 35 weight percent based on total weight of the first mixture. In yet another embodiment, the oxydiphthalic anhydride is present in the first mixture in an amount corresponding to at least 50 weight percent based on total weight of the first mixture. Typically, the first mixture is a slurry in which a portion of the oxydiphthalic anhydride is dissolved in the solvent and a portion of the oxydiphthalic anhydride is present as a solid phase of the slurry. Owing to their generally poor solubility, the alkali metal halides and alkaline earth metal halides typically remain as solids within the first mixture. It will be understood by those skilled in the art that the word "mixture" as used herein refers to a combination of at least two components at least one of which is at least partially insoluble in the other, or a "slurry". Thus each of the first mixture, the second mixture and the third mixture comprises at least one component which is at least partially insoluble. For example, in the third mixture, although substantially all of the oxydiphthalic anhydride has been dissolved in the solvent, at least a portion of the inorganic salt remains insoluble and is present as a solid phase component of the mixture. Typically, the inorganic salt is highly insoluble in the third mixture.

In one embodiment, a first mixture provided in step (a) is diluted with at least one solvent in step (b) to provide a second mixture having a solids content of 10 to 30 weight percent based on total weight of the second mixture. In another embodiment, the solids content is 10 to 20 weight percent based on total weight of the second mixture. In yet another embodiment, the solids content is 10 to 15 weight percent based on total weight of the second mixture. In one embodiment the solvent employed in diluting the first mixture is ortho-dichlorobenzene. In alternate embodiments the solvent employed is at least one solvent selected from the group consisting of chlorobenzene, para-dichlorobenzene, 2,4-dichlorotoluene, 1,2,4-trichlorobenzene, diphenyl sulfone, phenetole, anisole, veratrole, toluene, xylene, mesitylene and mixtures thereof. In yet another embodiment the solvent employed comprises ortho-dichlorobenzene and at least one other aromatic solvent.

More particularly, dilution of the first mixture to form the second mixture of step (b) is accomplished using recycled solvent obtained from at least one previous batch of second mixture, or another mixture in the purification process.

In one embodiment, substantially all of the oxydiphthalic anhydride present in the second mixture of step (b) is not dissolved in the solvent. In one embodiment, at least 90 percent of the oxydiphthalic anhydride is not dissolved. In another embodiment, at least 95 percent of the oxydiphthalic anhydride is not dissolved. In yet another embodiment, at least 98 percent of the oxydiphthalic anhydride is not dissolved. Suitable solvents include those discussed herein, for example ortho-dichlorobenzene, anisole, and chlorobenzene. Typically, a single solvent is employed in each of steps (a) to (f). Ortho-dichlorobenzene is in certain instances a preferred solvent.

In step (c), the second mixture, a solid-liquid slurry, is filtered at a temperature below the crystallization point temperature of the oxydiphthalic anhydride. As is understood by those skilled in the art, the crystallization point temperature is a function of a number of parameters including the concentration of the dissolved oxydiphthalic anhydride in the solvent, the properties of the solvent, the structure of the oxydiphthalic anhydride, and the state of purity of the oxydiphthalic anhydride (for example, mixtures of isomeric oxydiphthalic anhydrides versus single isomer oxydiphthalic anhydrides). The crystallization point temperature is typically in a range from about −15° C. to about 200° C. Typically, the filtration device is a porous filter which is maintained at a temperature below the crystallization point temperature of the oxydiphthalic anhydride. The filtration step yields a filter cake (also referred to as wet cake, or simply cake), that can include oxydiphthalic anhydride, inorganic salt, and impurities such as unreacted monomers and residual catalyst. In one embodiment the filtering is carried out at a temperature in a range from about 0° C. to about 50° C., in another embodiment from about 15° C. to about 40° C., and in yet another embodiment from about 20° C. to about 30° C. Most particularly filtering is carried out at ambient temperature. Typically, the filtering is carried out at (0 PSIG) or near (5 to 25 PSIG) atmospheric pressure under an inert atmosphere, for example under a nitrogen atmosphere. The filter cake is washed with solvent to provide a mother liquor, a wash liquor, and the third mixture comprising oxydiphthalic anhydride (ODPA) and salt. The amount of wash solvent ranges from 1 to 4 times the amount of ODPA, more particularly 2 to 3 times the amount of ODPA. The wash solvent can be non-recycled solvent and/or recycled mother liquor and/or wash liquor obtained from a previous batch of second mixture, or recycled solvent obtained from another mixture in the purification process. The mother liquor and wash liquor produced by the filtration can be directed to separate or common storage vessels for further recycling as described above.

Filtering in step (c) can be carried out employing methods known in the art. Exemplary filtration units include FUNDA-BAC® filtration units sold by DrM Incorporated (referred to herein as a DrM filtration unit), a centrifugal filtration unit, filter press, nutsche, rotary drum filter, or belt filter. In one embodiment, filtering is carried out by means of a metal filter. In one embodiment, filtering is carried out by means of a ceramic filter. In one embodiment, filtering is carried out by means of a sintered metal filter. In one embodiment, filtering is carried out by means of a porous candle wrapped in cloth media, as in a DrM filtration unit. The filter pore size ranges from 0.1 to 50.0 micrometers. In various embodiments, the filter employed has a pore size in a range from about 0.1 micrometers to about 20 micrometers, more particularly from about 0.5 micrometers to about 10 micrometers, and most particularly from about 5 micrometers to 10 micrometers.

In step (d) the oxydiphthalic anhydride of the third mixture is hydrolyzed to the corresponding oxydiphthalic tetraacid (ODTA) by addition of (1) a water-soluble acid having a pKa less than or equal to the pKa of oxydipthalic tetraacid and (2) water to the third mixture, forming a fourth mixture and heating the fourth mixture to form the ODTA. In one embodiment the water of step (d) is recycled water from a component selected from the group consisting of mother liquor, wash liquor, and combinations thereof; from step (d) obtained from a previous batch of fifth mixture. The heating temperature ranges from 80° C. to 130° C., in particular 85° C. to 120° C., and more particularly 90° C. to 110° C., and most particularly 95° C. to 105° C. In one embodiment, the amount of oxydiphthalic tetraacid in the fourth mixture of step (d) ranges from 5 to 30 weight percent based on total weight of the fourth mixture. In one embodiment, the amount of oxydiphthalic tetraacid in the fourth mixture ranges from 10 to 20 weight percent based on total weight of the fourth mixture. The time of the hydrolysis ranges from 1 to 10 hours, more particularly 2 to 8 hours, and most particularly 2 to 4 hours. Residual organic solvent trapped in the third mixture from step (c) can be removed by distillation during step (d), while replenishing lost water to maintain a constant percent solids in the hydrolysis reaction vessel. The acid of step (d) generally has a pKa less than 5, more particularly less than 4.5 and most particularly less than 2.5. Exemplary acids include phosphoric acid, sulfuric acid, boric acid, hydrochloric acid, hydrobromic acid, methane sulfonic acid, toluene sulfonic acid, trichloroacetic acid, and the like. In one embodiment, the acid of step (d) is phosphoric acid. The acid is used in an amount of about 0.2 to 20 mole equivalents, and more particularly one mole equivalent relative to ODPA. Hydrolysis followed by cooling to temperatures from −5° C. to 75° C. produces the fourth mixture comprising the ODTA as a solid-liquid slurry. The fourth mixture can optionally be decanted before filtration, whereupon the remaining solid-liquid mixture is rediluted with water. Filtering provides a mother liquor and solid component which is washed with water to provide wash liquor and the fifth mixture as a wet cake comprising oxydiphthalic tetraacid and water. In one embodiment, filtering in step (d) is by means of a DrM filtration unit, a centrifugal filtration unit, filter press, nutsche, rotary drum filter, or belt filter. The aqueous mother liquor and wash liquor obtained from the filtration can be directed to storage vessels for recycling. In one embodiment, the water wash liquor from step (d) is recycled one or more times. In one embodiment the water wash liquor from step (d) is recycled from one to 20,000 times. The ratio of wash water to ODTA ranges from 5:1 to 15:1 by weight, more particularly 8:1 to 12:1, and most particularly 10:1. Advantageously, the fifth mixture has a substantially lower level of inorganic salt impurity.

In step (e) the fifth mixture comprising oxydiphthalic tetraacid is heated at a temperature and a pressure sufficient to convert the oxydiphthalic tetraacid back to the oxydiphthalic anhydride. Step (e) can optionally be performed without addition of a solvent, in molten state or solid state, but typically this step includes an organic solvent selected from those previously described, in particular ortho-dichlorobenzene because of its azeotropic properties with the water formed during the condensation. The oDCB/water azeotrope is removed to form a sixth mixture comprising anhydrous oxydiphthalic anhydride. This mixture can be further filtered in step (f) while in solution to provide a substantially pure and anhydrous oxydiphthalic anhydride.

In step (f) the sixth mixture is filtered to obtain substantially pure oxydiphthalic anhydride. Filtering is accomplished by the above-described methods. In one embodiment, filtering in step (f) is by means of a filtration unit characterized by a filter pore size of 0.5 to 10 micrometers. In one embodiment, filtering in step (f) is by means of a filtration unit characterized by a filter pore size of 0.5 to 2 micrometers. In one embodiment, the substantially pure oxydiphthalic anhydride obtained in step (f) has insoluble impurities in an amount more than 0 and less than 150 ppm relative to the oxydiphthalic anhydride. Following the filtration step, the oxydiphthalic anhydride is cooled to obtain substantially pure crystalline oxydiphthalic anhydride. Typically the crystallization is effected using conventional techniques that are well known in the art at a temperature corresponding to the crystallization point temperature or a lower temperature. Thus, crystallization of the oxydiphthalic anhydride from the homogenous solution is typically effected at a temperature in a range from about −15° C. to about 200° C. In one embodiment, the crystallization is effected at a temperature in a range of from about −10° C. to about 120° C. In an alternate embodiment crystallization is effected at a temperature in a range from about 0° C. to about 80° C. Typically, the crystallization is effected in a vessel equipped with an agitator. When the crystallization step is effected under agitation, the product of the crystallization step is a slurry of the crystallized oxydiphthalic anhydride in the solvent. The crystallized oxydiphthalic is typically of significantly higher purity than the oxydiphthalic anhydride initially provided in step (a).

In one embodiment, the purified oxydiphthalic anhydride contains less than about 100 ppm, in another embodiment less than about 50 ppm, in yet another embodiment less than about 30 ppm, and in still yet another embodiment less than about 10 ppm of alkali metal ions, alkaline earth metal ions, or mixtures thereof. In another embodiment, the product of the purification method is a purified slurry of oxydiphthalic anhydride in at least one solvent, the slurry containing less than about 100 ppm, in another embodiment less than about 50 ppm, in yet another embodiment less than about 30 ppm, and in still yet another embodiment less than about 10 ppm of alkali metal ions, alkaline earth metal ions, or mixtures thereof. In one embodiment, the purified 4,4'-oxydipthalic anhydride contains insoluble material in an amount that is more than 0 and less than 150 ppm, relative to the 4,4'-oxydiphthalic anhydride. In another embodiment, the substantially pure oxydiphthalic anhydride contains less than 30 ppm potassium, less than 4000 ppm chlorophthalic anhydride, and less than 30 ppm catalyst, based on total weight of the oxydiphthalic anhydride in the sixth mixture.

Also disclosed is an oxydiphthalic anhydride purified by the above described method, wherein the sixth mixture from step (f) comprises less than 50 ppm alkali metal ion, less than 1000 ppm chlorophthalic anhydride, and less than 30 ppm catalyst, based on total weight of the oxydiphthalic anhydride in the sixth mixture; and the at least one solvent of step (b) is recycled mother liquor and wash liquor from step (c) obtained from a previous batch of first mixture.

Also disclosed is a method for purifying 4,4'-oxydiphthalic anhydride having structure (II), the method comprising steps (a) to (f):

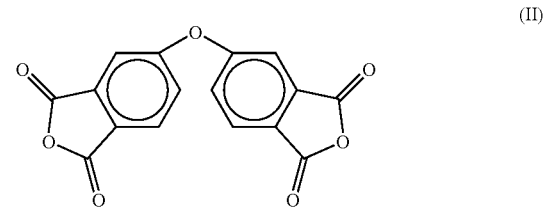

(II)

(a) providing a first mixture comprising 4,4'-oxydiphthalic anhydride, ortho-dichlorobenzene, at least one catalyst including hexaethylguanidinium chloride, and potassium chloride, the 4,4'-oxydiphthalic anhydride being present in the first mixture in an amount of 10 to 30 percent by weight based on total weight of the first mixture;

(b) diluting the first mixture with ortho-dichlorobenzene to provide a second mixture having a solids content of 10 to 30 percent based on total weight of the second mixture;

(c) filtering the second mixture at a temperature of 5° C. to 150° C. and washing the solids with ortho-dichlorobenzene to provide a mother liquor, a wash liquor, and a third mixture of the 4,4'-oxydiphthalic anhydride and potassium chloride;

(d) hydrolyzing by adding phosphoric acid and water to the third mixture, forming a fourth mixture, and heating the fourth mixture and subsequently cooling the fourth mixture, wherein a portion of the liquid of the fourth mixture is decanted, rediluted with water, filtered and washed with water to provide wash liquor and a fifth mixture of 4,4'-oxydipthalic tetraacid and water;

(e) ring closing the 4,4'-oxydiphthalic tetraacid by heating the fifth mixture under a temperature and pressure sufficient to convert the 4,4'-oxydiphthalic tetraacid to the 4,4'-oxydiphthalic anhydride, forming a sixth mixture; and (f) filtering the sixth mixture to obtain substantially pure 4,4'-oxydiphthalic anhydride.

Also disclosed is a method of preparing a purified oxydiphthalic anhydride, comprising contacting in a reaction mixture at least one substituted phthalic anhydride of formula (III)

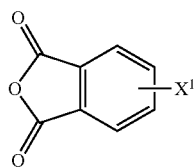

(III)

wherein $X^1$ is selected from the group consisting of fluoro, chloro, bromo, iodo, and nitro groups, at least one aprotic solvent, at least one catalyst, and at least one inorganic carbonate to provide a product mixture comprising a product oxydiphthalic anhydride of formula (I) in an amount corresponding to at least 25 weight percent of the total weight of the product mixture.

Exemplary substituted phthalic anhydrides include, 3-chlorophthalic anhydride, 4-chlorophthalic anhydride, 3-fluorophthalic anhydride, 4-fluorophthalic anhydride, 4-nitrophthalic anhydride, 3-nitrophthalic anhydride, and mixtures thereof.

Exemplary catalysts are known in the art; reference is made, for example, to U.S. Pat. No. 5,081,298. Typical catalysts include hexaalkylguanidinium halides, pyridinium halides, phosphonium salts, phosphazenium salts and the like. Representative hexaalkylguanidinium halides are illustrated by formula (IV); while representative pyridinium halides are shown in formula (V); and representative phosphazenium catalysts are shown in formula (VI).

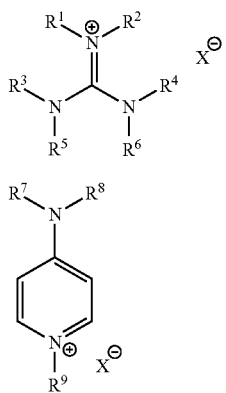

(IV)

(V)

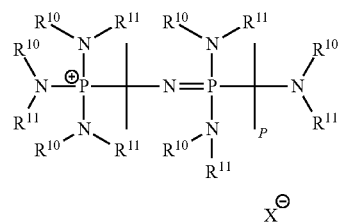

(VI)

In structures (IV), (V), and (VI), $R^1$-$R^{11}$, independently represent a $C_1$-$C_{20}$ aliphatic radical, a $C_3$-$C_{40}$ aromatic radical, or a $C_3$-$C_{20}$ cycloaliphatic radical; and $X^-$ is a monovalent inorganic anion, a monovalent organic anion, a polyvalent inorganic anion, polyvalent organic anion, or a mixture thereof. With respect to structure VI, "p" is an integer from zero to 10. In structures (IV), (V), and (VI), two or more of the groups represented by $R^1$-$R^{11}$, when present in the same structure, may be linked together form a cyclic structure comprising at least one nitrogen atom. Exemplary catalysts having general structure (IV) are illustrated by hexaethylguanidinium mesylate, hexaethylguanidinium chloride, hexaethylguanidinium bromide, hexaethylguanidinium acetate, and combinations thereof. Exemplary catalysts having general structure (V) are illustrated by 1-neopentyl-4-(N,N-dibutylamino)-pyridinium chloride, 1-neopentyl-4-piperidin-1-ylpyridinium chloride, 1-neopentyl-4-piperidin-1-ylpyridinium mesylate, 1-3-methylheptyl-4-(4-methyl)-piperidin-1-ylpyridinium chloride, and combinations thereof. Exemplary catalysts having general structure (VI) are illustrated by octamethylphosphazenium chloride (p=0), octamethylphosphazenium bromide (p=0), dodecamethylphosphazenium chloride (p=1), dodecamethylphosphazenium mesylate (p=1), and mixtures thereof. The amount of phase transfer catalyst is typically used in an amount corresponding to from about 0.1 mole percent to about 10 mole percent based on the total number of moles of substituted phthalic anhydride employed.

In one embodiment, the catalyst is a guanidinium salt of the structure (VII)

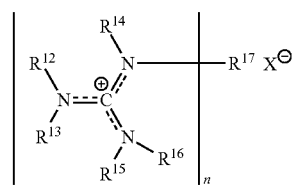

(VII)

wherein each of $R^{12}$, $R^{13}$, $R^{14}$, $R^{15}$, $R^{16}$ and $R^{17}$ is independently $C_1$-$C_{20}$ aliphatic radical, a $C_3$-$C_{40}$ aromatic radical, or a $C_3$-$C_{20}$ cycloaliphatic radical. In addition, at least two or more of $R^{12}$, $R^{13}$, $R^{14}$, $R^{15}$, $R^{16}$ and $R^{17}$ may together form a cycloaliphatic radical or an aromatic radical comprising at least one nitrogen atom. The anionic species, $X^-$, represents one or more monovalent inorganic anions, monovalent organic anions, polyvalent inorganic anions, polyvalent organic anions, and mixtures thereof. "n" is 1 or 2. Exemplary catalysts having structure (VII) include the bisguanidinium salt wherein $R^{12}$, $R^3$, $R^{14}$, $R^{15}$, and $R^{16}$ are methyl groups, $R^{17}$ is a 1,3-propanediyl radical (i.e., —$CH_2CH_2CH_2C_2$—), "n" is 2, and $X^-$ represents two chloride anions.

In one embodiment the inorganic carbonate salt has a structure (VIII)

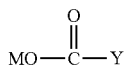 (VIII)

wherein M is a metal ion selected from the group consisting of alkali metal ions, alkaline earth metal ions, and mixtures thereof, and Y is OM or OH. In one embodiment the metal ion M is lithium, sodium, potassium, or a mixture thereof. Exemplary inorganic carbonates include potassium carbonate, sodium carbonate, potassium sodium carbonate, lithium carbonate, potassium lithium carbonate, sodium lithium carbonate, potassium bicarbonate, sodium bicarbonate, lithium bicarbonate, or mixtures thereof.

Typically, the amount of inorganic carbonate and the substituted phthalic anhydride (III) are employed in amounts corresponding to a ratio of the inorganic carbonate to substituted phthalic anhydride in a range from about 1.0 moles to about 1.5 moles of inorganic carbonate to about 1 mole of substituted phthalic anhydride.

The reaction, sometimes referred to herein as "contacting," of the substituted phthalic anhydride (III) in an aprotic solvent, at least one inorganic carbonate and the catalyst, is typically carried out by heating the reactants and solvent in a stirred reactor. In one embodiment, the reaction mixture is heated to a temperature in a range from about 50° C. to about 250° C. The reactor can be equipped with a means for removing solvent by distillation, such as a distillation head, condenser and receiver. Solvent may be distilled from the reaction mixture during the reaction or upon its completion as a means for removing adventitious water or water produced during the reaction. The reaction results in a product mixture comprising the oxydiphthalic anhydride product and solvent together with an inorganic salt by-product of the reaction. The identity of the salt by-product is determined by the inorganic carbonate employed as well as the nature of the substituent leaving group in the substituted phthalic anhydride ($X^1$ in structure (III)). For example, when the substituted phthalic anhydride is 4-nitrophthalic anhydride and the inorganic carbonate is sodium carbonate, the salt by-product is sodium nitrite. As a further example, when the substituted phthalic anhydride is 4-chlorophthalic anhydride and the inorganic carbonate is potassium carbonate, the salt by-product is potassium chloride. Typically, the oxydiphthalic anhydride product is present in the product mixture in an amount corresponding to at least 25 weight percent based on total weight of the product mixture. Moreover, the product mixture typically comprises less than about 100 ppm water. The oxydiphthalic anhydride is then purified by diluting the product mixture with at least one solvent, to provide a second mixture wherein the oxydiphthalic anhydride is present in an amount corresponding to less than 25 weight percent based on total weight of the second mixture. The reaction mixture is then either heated or further diluted to dissolve substantially all of the oxydiphthalic anhydride present in the second mixture thereby providing a third mixture comprising less than 25 ppm water, and wherein the oxydiphthalic anhydride is present in an amount corresponding to less than 25 weight percent based on total weight of the third mixture. The third mixture is then filtered to remove the inorganic salt by-product. This filtration is carried out at a temperature above the crystallization point temperature of the oxydiphthalic anhydride and provides in addition to a filter cake comprising the inorganic salt by-product, a filtrate. In one embodiment, the filtration is carried Out at a temperature in a range between about 100° C. and about 180° C. The filtrate is initially a homogeneous solution comprising the oxydiphthalic anhydride product and solvent. In one embodiment, the oxydiphthalic anhydride is crystallized from the homogeneous solution to provide a purified oxydiphthalic anhydride containing less than 100 ppm of alkali metal ions, alkaline earth metal ions, or mixtures thereof.

Also disclosed is a method for preparing a polyetherimide derived from an oxydiphthalic anhydride purified by the disclosed purification method. The method comprises combining at least one solvent, at least one oxydiphthalic anhydride purified by the disclosed purification method, and at least one diamino aromatic compound to form a polymerization mixture under art recognized conditions suitable for the condensation polymerization of an oxydiphthalic anhydride with at least one aromatic diamine. Typically, such conditions involve heating a solution of roughly equal molar amounts of the oxydiphthalic anhydride and the aromatic diamine in the presence of an optional imidization catalyst such as sodium phenyl phosphinate (SPP, $C_6H_5PO_2Na$). The polymerization reaction is generally conducted under conditions such that the solvent is continuously refluxing. A trap such as a Dean-Stark trap or a suitable decant system, may be employed to separate water formed during the condensation polymerization. In general, the polymerization reaction is most efficient and higher molecular weight polyetherimide product is obtained when as much water as possible is removed from the reaction mixture.

In one embodiment, the at least one aromatic diamine is represented by formula (IX)

 (IX)

wherein B is a $C_3$-$C_{30}$ divalent organic radical. In one embodiment B is a monocyclic divalent aromatic radical, for example para-phenylene. In an alternative embodiment B is a polycyclic divalent aromatic radical, for example 4,4'-biphenylene or 1,4-naphthalene.

In one embodiment B is a $C_3$-$C_{30}$ divalent aromatic radical having formula (X)

 (X)

wherein the unassigned positional isomer about the aromatic ring is either meta or para to Q, and Q is a linking group chosen from

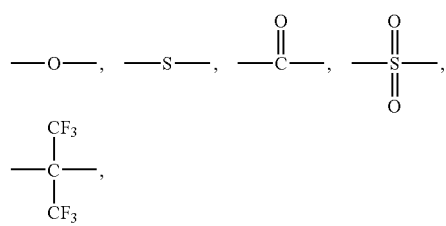

a covalent bond, an alkylene group of the formula $C_yH_{2y}$, or an alkylidene group of the formula $C_yH_{2y}$; wherein "y" is an integer from 1 to 5 inclusive. In one embodiment, Q is a divalent aromatic radical such as bis-Phenol A. In some particular embodiments "y" has a value of one or two. Illustrative alkylene and alkylidene linking groups Q include, but are not limited to, methylene, ethylene, ethylidene, propylene, and isopropylidene. In other particular embodiments the unassigned positional isomer about the aromatic ring in formula (X) is para to Q.

In various embodiments the two amino groups present in the aromatic diamine (IX) are separated by at least two and sometimes by at least three ring carbon atoms. When the amino group or groups are located in different aromatic rings of a polycyclic aromatic moiety, they are often separated from the linking group between any two aromatic rings by at least two and sometimes by at least three ring carbon atoms.

Exemplary aromatic diamines of formula (IX) include 2-methyl-1,3-diaminobenzene; 4-methyl-1,3-diaminobenzene; 2,4,6-trimethyl-1,3-diaminobenzene; 2,5-dimethyl-1,4-diaminobenzene; 2,3,5,6-tetramethyl-1,4-diaminobenzene; 1,2-bis(4-aminoanilino)cyclobutene-3,4-dione, bis(4-aminophenyl)-2,2-propane; bis(2-chloro-4-amino-3,5-diethylphenyl)methane, 4,4'-diaminodiphenyl, 3,4'-diaminodiphenyl, 3,3'-diaminodiphenyl, 3,3'-dimethyl-4,4'-diaminodiphenyl, 3,3'-dimethoxy-4,4'-diaminodiphenyl, 2,2',6,6'-tetramethyl-4,4'-diaminobiphenyl; 3,3'-dimethoxy-4,4'-diaminobiphenyl; 4,4'-diaminodiphenylmethane, 3,3'-diaminodiphenylmethane, 3,4'-diaminodiphenylmethane, 1,3-bis(3-aminophenoxy)benzene, 1,3-bis(4-aminophenoxy)benzene, 1,4-bis(4-aminophenoxybenzene), bis(4-(4-aminophenoxy)phenyl)sulfone, bis(4-(3-aminophenoxy)phenyl)sulfone, 4-(4-aminophenoxy)phenyl)(4-(3-aminophenoxy)phenyl)sulfone, 4,4'-bis(3-aminophenoxy)biphenyl, 4,4'-bis(4-aminophenoxy)biphenyl, 4-(3-aminophenoxy)-4'-(4-aminophenoxy)biphenyl, 2,2'-bis(4-(4-aminophenoxy)phenyl)propane, 2,2-bis[4-(4-aminophenoxy)phenyl]hexafluoropropane, 4,4'-bis(aminophenyl)hexafluoropropane, 4,4'-diaminodiphenyl ether, 3,4'-diaminodiphenyl ether, 3,3'-diaminodiphenyl ether, 4,4'-diaminodiphenylsulfide, 3,4'-diaminodiphenylsulfide, 3,3'-diaminodiphenylsulfide, 3,3'-diaminodiphenylsulfone, 4,4'-diaminodiphenyl sulfone, 3,4'-diaminodiphenyl sulfone, 4,4'-(9-fluorenylidene)dianiline; 4,4'-diaminodiphenyl ketone, 3,4'-diaminodiphenyl ketone, 3,3'-diaminodiphenyl ketone, 2,6-diaminotoluene and 2,4-diaminotoluene.

In one embodiment, two or more aromatic diamines can also be used. For example, the ETHACURE diamines, available from Albemarle Corporation, Baton Rouge, La., such as ETHACURE 100, which is a 80:20 weight ratio combination of 2,6-diethyl-4-methyl-1,3-phenylene diamine and 4,6-diethyl-2-methyl-1,3-phenylene diamine, respectively; and ETHACURE 300, which is a 80:20 weight ratio combination of 2,6-bis(mercaptomethyl)-4-methyl-1,3-phenylenediamine and 4,6-bis(mercaptomethyl)-2-methyl-1,3-phenylenediamine, respectively, can also be used. Perfluorinated alkyl or partially fluorinated alkyl analogs of the diamines are also suitable for use.

Also disclosed is a polyetherimide derived from an oxydiphthalic anhydride purified by the disclosed method, wherein the sixth mixture from step (f) comprises less than 50 ppm alkali metal ion, less than 1000 ppm chlorophthalic anhydride, and less than 30 ppm catalyst, based on total weight of the oxydiphthalic tetraacid present in the sixth mixture, and the at least one solvent of step (b) is recycled mother liquor and wash liquor from step (c) obtained from a previous batch of first mixture. In one embodiment, the polyetherimide is derived from 4,4'-oxydiphthalic anhydride purified by the disclosed method.

The described purification method, in addition to providing acceptable impurity levels, lowers water consumption by at least about 35% and lowers organic solvent usage by 13-fold, without sacrificing overall yield and quality of ODPA. In one embodiment, water consumption can lowered in an amount ranging from at least 35% to about 80%.

Advantageously, this method provides previously unavailable benefits. For instance, the method now provides a single process that produces high quality oxydiphthalic anhydrides in conditions that contain materials with disparate solubility properties. Further, since the method can be practiced with reused/recycled solvents and produce high quality products, it is now possible to purify oxydiphthalic anhydrides economically and more efficiently, since the amount of solvent required to purify the oxydiphthalic anhydride is substantially reduced.

Although the method encompasses purifying an oxydiphthalic anhydride having structure (I):

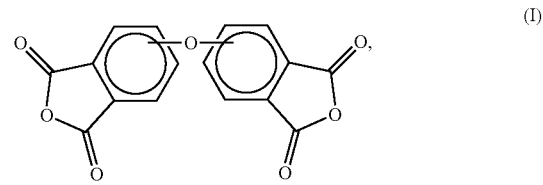

the method can be employed for purification of other bisanhydrides, for example the bisanhydride of formula (XI),

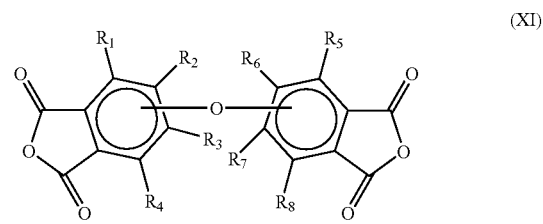

wherein $R^1$, $R^2$, $R^3$, $R^4$, $R^5$, $R^6$, $R^7$, and $R^8$ can each individually be selected from the following substituents:

hydrogen;

halogen radical, e.g., F, Cl, Br, I, and the like;

alkyl radicals, e.g., methyl, ethyl, hexyl, chloromethyl, and the like;

cycloaliphatic radicals, e.g., cyclopentyl, cyclohexyl, and the like;

aromatic radicals, e.g., phenyl, benzyl, 4-methyl-phenyl, xylyl, 3-bromo-phenyl, and the like;

—CN, —NO$_2$, —SH, —OH, ethers, —COR, aldehyde, ketone, esters, and the like; wherein when R is H, there is at least one other R group that is not H. In one embodiment, $R^1$, $R^2$, $R^3$, and $R^4$ form one half of the aryl ether linkage —O—, and $R^5$, $R^6$, $R^7$, and $R^8$ form the other half of the aryl ether linkage —O—.

As such, in another embodiment, the method encompasses purifying a dianhydride having formula (XII),

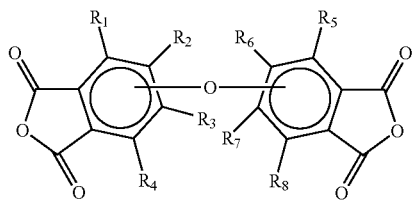

(XII)

by:
(a) providing a first mixture comprising at least one dianhydride, at least one solvent, at least one catalyst, and at least one inorganic salt selected from the group consisting of alkali metal halide salts, alkaline earth metal halide salts, and mixtures thereof, the dianhydride being present in the first mixture in an amount of 10 to 30 percent by weight based on total weight of the first mixture;
(b) diluting the first mixture with at least one solvent, to provide a second mixture having a solids content of 10 to 30 percent based on total weight of the second mixture;
(c) filtering the second mixture at a temperature below the crystallization point temperature of the dianhydride and washing the solid with solvent to provide a mother liquor, a wash liquor, and a third mixture of the dianhydride and salts;
(d) hydrolyzing by adding (1) a water-soluble acid having a $pK_a$ less than or equal to the $pK_a$ of tetraacid and (2) water to the third mixture, forming a fourth mixture and heating the fourth mixture; wherein the fourth mixture is cooled to provide a solid-liquid mixture; optionally decanting a portion of the liquid, wherein the remaining solid-liquid mixture is rediluted with water; then filtered to provide a mother liquor and solid component; and the solid component is washed with water to provide wash liquor and a fifth mixture of tetraacid and water; and
(e) ring closing the tetraacid by heating the fifth mixture under a temperature and pressure sufficient to convert the tetraacid to the dianhydride, forming a sixth mixture; and
(f) filtering the sixth mixture to obtain a substantially pure dianhydride.

The following non-limiting examples further illustrate the practice of the method.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, and temperature is in degrees Celsius (° C.).

Example 1

Preparation of 4,4'-oxydiphthalic anhydride (4,4'-ODPA or ODPA). The synthesis of 4,4'-ODPA from 4-chlorophthalic anhydride, $K_2CO_3$ and catalysts, such as HEGCl, produce various side products which need to be removed before the monomer 4,4'-ODPA can be used in a polymerization. After dilution of the reaction mixture with oDCB, the subsequent filtration step was conducted to simulate a DrM filtration unit, which required large amounts of solvent to dilute the feed to the filter unit and to pre-fill the filter unit. To minimize the oDCB utilization, the filtrate from the first filtration, termed mother liquor (ML), or the filtrate from the wash step termed wash liquor (WL), or the combination of the two was recycled for dilution of subsequent batches of the 4,4'-ODPA reaction mixture. The filtered solid is referred to as the wet cake (WC). This example describes the effectiveness of recycling the combined ML and WL for the purpose of reducing solvent usage.

Reagent grade ortho-dichlorobenzene (oDCB) was used as received from Fisher Scientific. Material used in the glove box had been stored over 4 A molecular sieves and checked for water levels of less than 10 ppm via KF (described below). Solid 4-ClPA was obtained and was further purified by distillation. HEGCl in brine solution was used. $K_2CO_3$ was obtained and dried at 220° C. in a Kugelrohr overnight, then stored in the glove box. Extra fine particle size was used, identical to material used on a greater than 100 gal (379 liter) scale. The 85% $H_3PO_4$ was used as received from Fisher Scientific.

Karl-Fischer Titration (KF) was used to measure water content in the 4,4'-ODPA prepared above. A sample of about 5 milliliter of solvent was obtained (normally from an oDCB distillate) taking care to ensure that the sample was dry. The plastic 1 milliliter gas-tight syringe was rinsed at least 3 times with the solvent to be checked, discarding each rinse. The syringe was carefully filled with the solvent and was then injected into the KF titrator. The analyzer carried out the titration automatically and results are recorded in ppm water.

The following lab procedure was used for the 4,4'-ODPA reaction. All glassware was thoroughly dried in an oven at 120° C. prior to use. The HEGCl brine solution, 5.2 milliliter, (1.86 grams HEGCl) and about 260 grams of oDCB was charged to a 250 milliliter three-neck round-bottom flask, which was equipped with a Dean-Stark trap with a condenser, a mechanical stirrer, and a nitrogen inlet. The mixture was azeotropically dried to remove water and 120 grams solvent. The dryness was confirmed by KF titration. The reaction apparatus was transferred to a dry box with inert conditions to transfer flaked 4-ClPA (32.85 grams; 0.180 mol, stored in glove box) and 12.10 grains $K_2CO_3$ (0.088 mol; Kugelrohr dried; stored in glove box). The mixture was heated at reflux (210° C. oil bath temperature) for 4 hours under nitrogen atmosphere with 50 grams of oDCB being distilled off. Reaction dryness was determined by sampling distillate as <10 ppm via KF. Several batches of ODPA were prepared using the starting materials and amounts listed in Table 1. All batches were combined as one standard 4,4'-ODPA reaction mixture.

TABLE 1

4,4'-ODPA Reaction Charges

| Batch | oDCB Charge (grams) | 4-ClPA Charge (grams) | $K_2CO_3$ Charge (grams) | HEGCl brine solution Charge (milliliter) |
|---|---|---|---|---|
| mlk0589-44 | 262.34 | 32.88 | 12.12 | 5.20 |
| mlk0589-43 | 262.36 | 32.85 | 12.11 | 5.20 |
| mlk0589-42 | 261.80 | 32.88 | 12.04 | 5.20 |
| mlk0589-41 | 261.36 | 32.31 | 12.13 | 5.20 |
| mlk0589-39 | 261.78 | 32.91 | 12.04 | 5.20 |
| mlk0589-38 | 262.92 | 32.88 | 12.04 | 5.20 |

Simulation of DrM with Recycling Mother Liquor and Wash Liquor:

A 25 gram portion of the standard 4,4'-ODPA reaction mixture was diluted to 15% solids by adding 32.74 grams of oDCB. The 15% solids solution was filtered on a 41 mm Buchner filter using Whatman #4 paper. The WC was then washed with 2 equivalents of fresh oDCB relative to the weight of 4,4'-ODPA. The mother liquor and wash liquor were combined. The combined mother and wash liquor was then used to dilute the next reaction mixture, which was from the same 4,4'-ODPA stock solution. The procedure was repeated 8 times, always combining the ML and WL. The WC's were then analyzed by HPLC.

The combined ML and WL were recycled for diluting the reaction mixture to 15 wt % solids. The repeated addition of WL (relatively clean oDCB) to the ML exposes the WC to a smaller fraction of the total impurities, whereas recycling only the ML exposes the WC to the total additive quantity of impurities.

Figure 2:
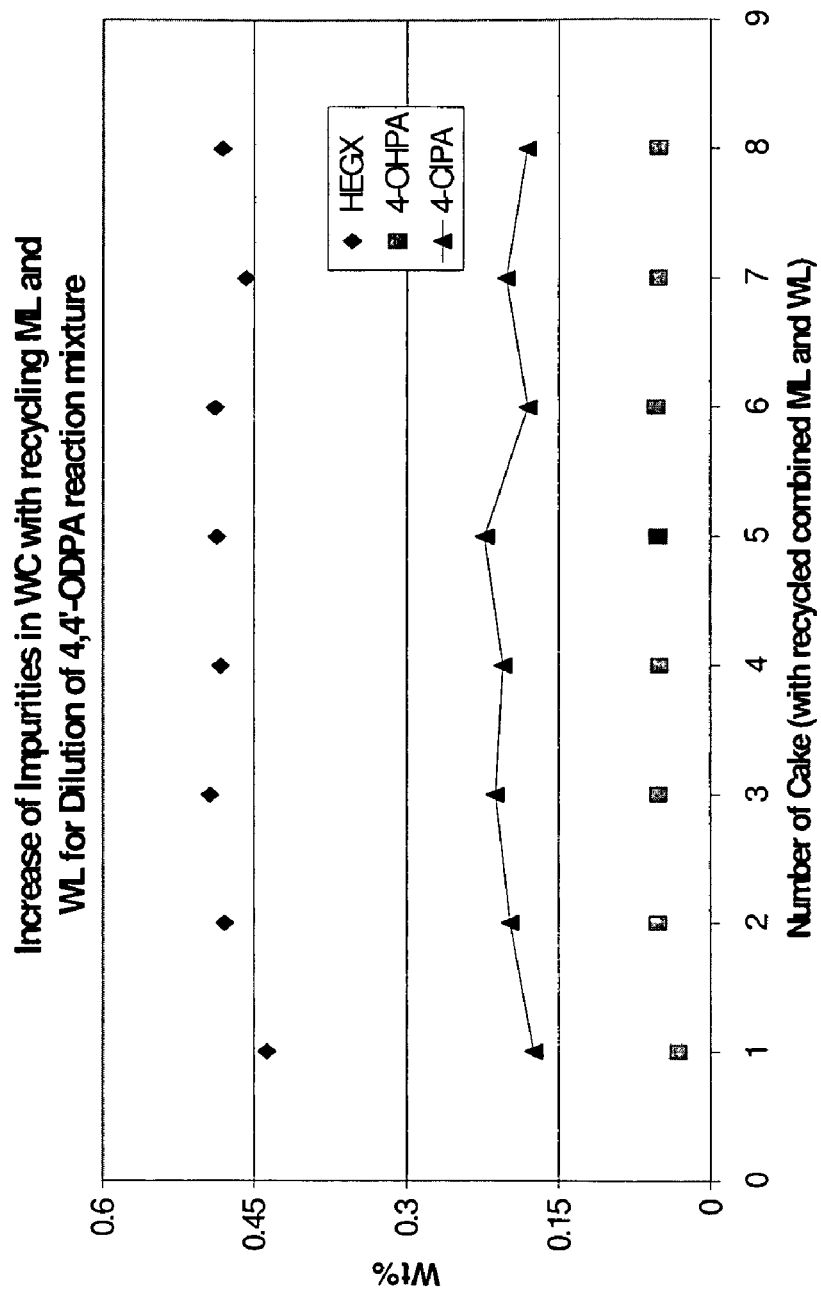
FIG. 2 is graph plotting the weight percent (wt %) of the impurities in wet cakes ("WC")s, where the number of the WC corresponds to the number of recycles of combined mother liquor (ML) and wash liquor (WL) at 15% solids dilution level.
Figure 3:
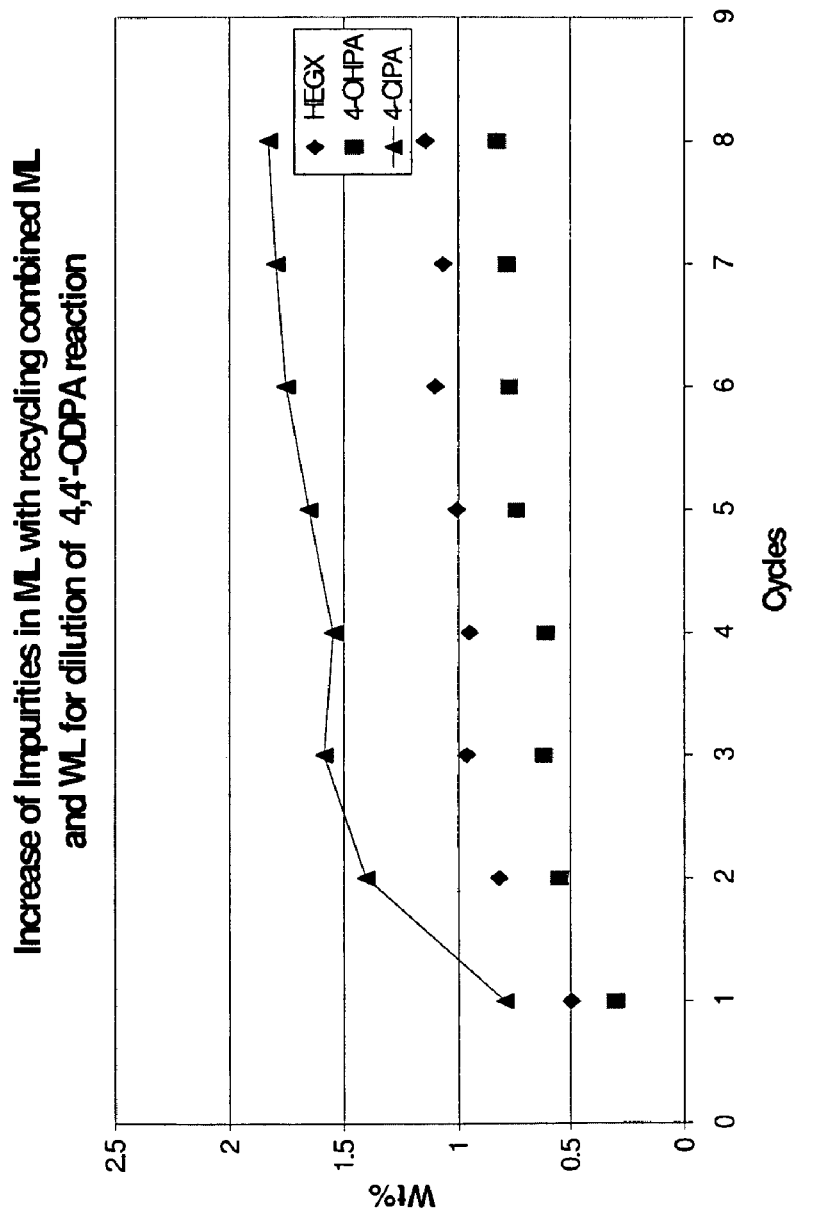
FIG. 3 is a graph plotting the weight percent of impurities in the mother liquor as a function of cycles of combined ML and WL at 15% solids dilution.

Diluting the 4,4'-ODPA reaction mixture to 15 wt % solids using recycled combined ML and WL resulted in relatively constant impurity levels in the WC after two cycles. The initial HEGCl concentration was 0.43 wt % and leveled off at approximately 0.47 wt % (FIG. 2). The initial 4-CIPA concentration was 0.17 wt % and leveled off at approximately 0.25 wt %. The initial 4-OHPA (hydroxyphthalic anhydride) concentration was 0.04 wt % and leveled off at approximately 0.05 wt %. All impurity values were normalized to the concentration of ODPA species in order to correct for the difference in the WC dryness. WC produced from the dilution of fresh oDCB was consistently between 0.3 wt % to 0.5 wt % HEGCl and 0.2 wt % to 0.3 wt % 4-CIPA, demonstrating the effectiveness of recycling the ML and WL for dilution. In FIG. 3, the impurity levels in the mother liquor for 15% solids dilution was plotted versus the number of cycles, and this shows a gradual increase up to cycle 6 where it then levels off. The impurity level in recycled combined ML and WL is considerably higher than the impurity level found in the corresponding WC, also demonstrating the effectiveness of the wash.

DrM Filtration Equipment Operation:

DrM is filtration equipment for removing solids from liquid. The filter media is cloth, which is wounded on metal candles. These candles are installed in a metal filter housing. The number of candles installed governs the total surface area/capacity of the filter. The following steps, illustrate a typical filtration process in a DrM filtration system, with numbers in parentheses corresponding to the parts in FIG. 1:

1) The ODPA reaction slurry (14) to be filtered is fed to the DrM feed tank (10) and diluted with fresh (16) or recycled solvent (28, 26).
2) The DrM filtration unit (12) is filled (36) with the fresh solvent, oDCB. The slurry (14) is then fed from the feed tank (10) to the DrM filtration unit (12) and re-circulated back (44) to the feed tank (10). This step ensures that the solids are well mixed and the filter is conditioned.
3) Next the equilibrated slurry goes through the filter (12) and the WC is formed on the candles of the DrM filtration unit (12). The mother liquor is circulated back (44) to the feed tank (10). This ensures efficient capturing on the WC of all the solids in the slurry.
4) The mother liquor is then transferred (18) to the mother liquor tank (34) and used for pre-filling the DrM filtration unit (12) for subsequent batches. DrM holdup is transferred (44) back to the feed tank (10) for diluting the next batch.
5) The DrM filtration unit (12) is then filled with the fresh solvent (36) and the WC is washed with the fresh solvent. The wash liquor is routed (20) to the mother liquor tank (34) and the DRM holdup is collected in a blow down tank (or wash liquor tank 24 of FIG. 1) and is used for filling the DrM for subsequent washing.
6) The cake is then dried and collected in drums.

The following examples utilize solvent recycling in the DrM filtration system to separate the solids from the slurry. The slurry fed to the DrM was a mixture of 4,4'-ODPA, KCl, 4-CIPA, and HEGCl in oDCB. 4,4'-ODPA and KCl are insoluble while 4-CIPA and HEGCl are soluble in oDCB. The isolated WC was composed of 4,4'-ODPA and KCl, with 4-CIPA and HEGCl as impurities. The target impurity levels for 4,4'-ODPA in the WC were: 4-CIPA less than 5000 ppm, and HEGCl less than 3000 ppm when normalized with 4,4'-ODPA. The objective was to achieve these impurity levels at minimum oDCB usage. High oDCB usage lowers the production yield. As shown below, oDCB usage can be lowered by recycling the ML and WL streams as demonstrated in the following examples.

The slurry fed to the DrM was obtained after the reaction step and had the following composition: 4,4'-ODPA about 14 wt %, KCl about 7 wt %, HEGCl about 2 wt % and 4-CIPA about 3 wt %, each based on the total weight of the slurry, and the remainder oDCB. Fresh oDCB was used as available on a greater than 500 gal (1893 liter) scale.

4500 parts of slurry was transferred to the filter feed tank where it was diluted to about 10 wt % solids based on total weight of the slurry with the mother liquor in the feed tank from a previous filter batch. The DrM was pre-filled with 8000 parts of mother liquor from the ML tank. The slurry was then re-circulated through the DrM and back to the feed tank. After conditioning the DrM in this manner, the solids were filtered. The ML was sent to the ML tank and the DrM holdup was recycled back to the feed tank. The DrM was then pre-filled with 8000 parts of oDCB from the blow down tank (oDCB from a previous batch), and the WC was washed with 1400 parts of fresh oDCB. The wash liquor, 1900 parts, was sent to the ML tank and the DrM holdup was sent to the blow down tank. The WC was then dried, collected, and analyzed for residual HEGCl and 4-CIPA using HPLC.

Figure 4:
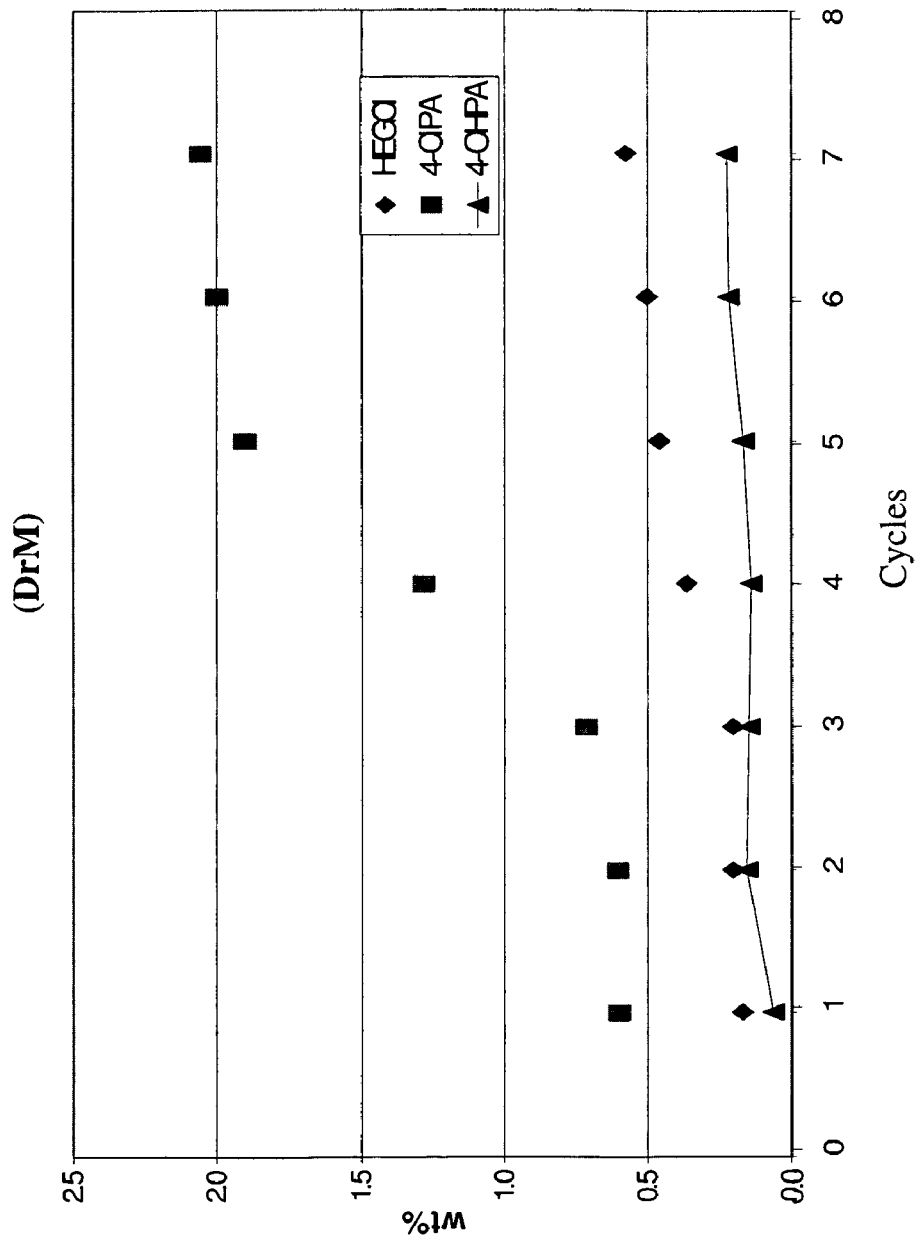
FIG. 4 is a graph plotting the weight percent of impurities in the mother liquor as a function of cycles, with combined ML and WL, on large scale, using a DrM filtration system. Each tick mark on the axis labeled "Cycles" is one cycle. Points are located above a tick mark.
Figure 5:
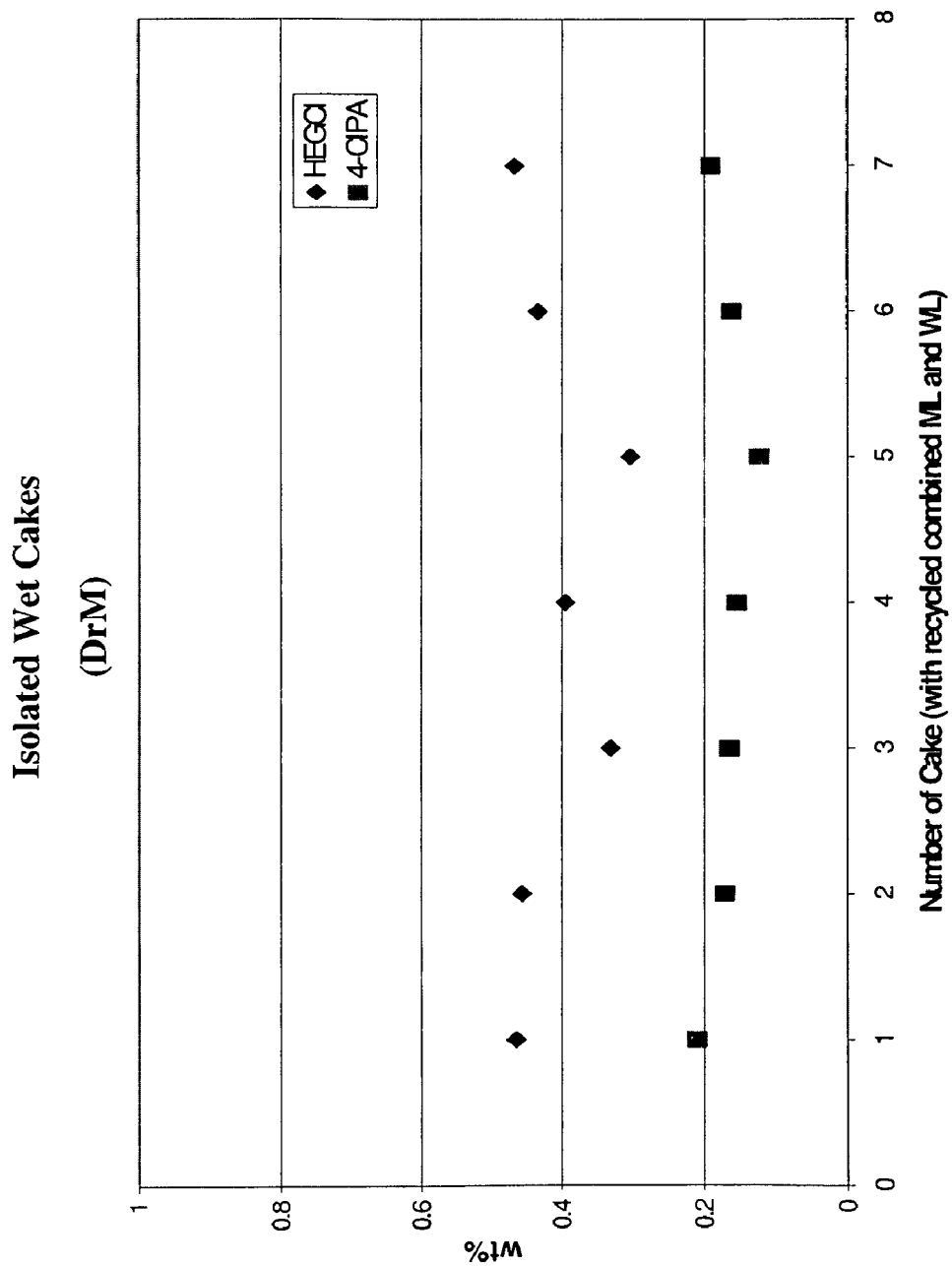
FIG. 5 is a graph plotting impurities in WCs as a function of recycling the combined ML and WL on large scale, using a DrM filtration system.

The 4-CIPA and HEGCl levels were measured at 3500 and 2400 ppm respectively. The fresh oDCB usage was 3 parts per part of ODPA using recycled ML and WL streams. Without recycling the streams, the amount was about 38 parts per part of ODPA. Hence recycling the streams reduced the oDCB usage by 13-fold. On large scale, the impurity levels in the combined recycled ML and WL gradually reached a plateau at concentrations (FIG. 4) comparable to the small scale lab simulations. The large scale isolated WCs also had impurity levels comparable to the small scale lab simulations. All the WCs consisted of between 0.3 wt % to 0.5 wt % HEGCl and 0.1 wt % to 0.3 wt % 4-CIPA (FIG. 5) based on total weight of the WC, corrected for solvent.

Figure 6:
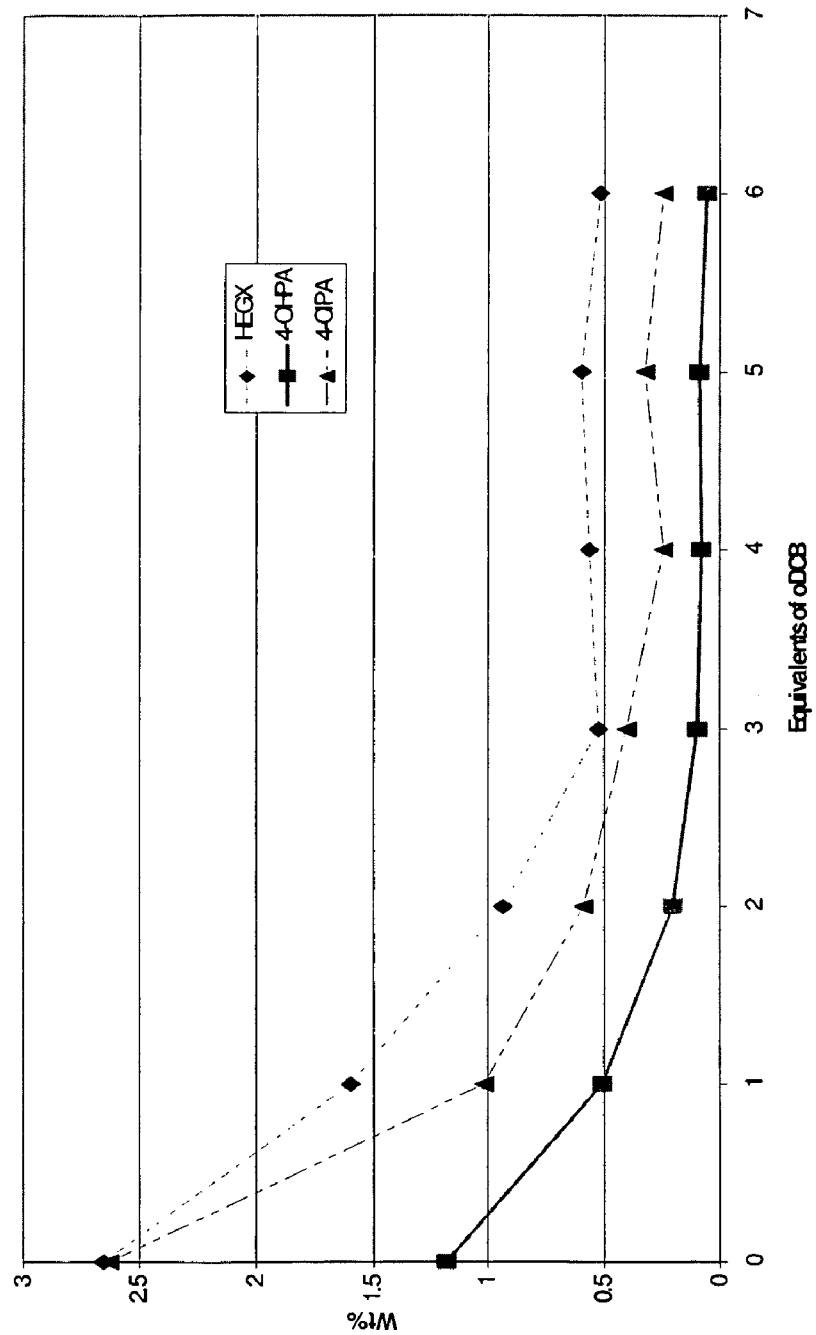
FIG. 6 is a graph plotting weight percent of impurities in the WC versus equivalents of ortho-dichlorobenzene washes on large scale using a DrM filtration system.

FIG. 6 shows that the impurity levels in the WC were not significantly reduced after four equivalents (by mass) of oDCB. The HEGCl was reduced to a minimum of about 0.5 wt %. The 4-CIPA was reduced to a level of 0.25 wt % after four equivalent washes based on total weight of the WC. The 4-OHPA leveled off at 0.1 wt % based on total weight of the WC after three equivalent washes.

Summarizing, recycling the ML and WL advantageously reduced oDCB usage by 13-fold, and also resulted in a 50% reduction in cycle time.

Example 2

The purpose of this Example was to show that without decantation, a relatively higher level of impurities levels were present in the 4,4'-oxydiphthalic anhydride that was produced, as compared to Examples 4 and 5 where decantation is practiced. 2645 parts of a WC of material consisting of 68.7 wt % 4,4'-oxydiphthalic anhydride, 13.3 wt % of potassium chloride, 18 wt % of ortho-dichlorobenzene based on total weight of the WC, and some minor impurities such as hexaethylguanidinium chloride (1146 ppm) and chlorophthalic anhydride (1591 ppm), was mixed with 528 parts of phosphoric acid (85 wt %) and 11877 parts of water and heated under vacuum until boiling, about 80° C. Under these conditions, 4,4'-oxydiphthalic anhydride and chlorophthalic anhydride react with the water to form 4,4'-oxydiphthalic tetraacid (ODTA) and chlorophthalic acid (CIDA). The oDCB was removed from the mixture as an azeotrope with water. The weight of the reactor was maintained constant by adding the corresponding amount of water back to the reactor. The process took approximately 25 hours. Subsequently, the mixture was cooled to 14° C. and centrifuged. The WC was washed with 10 parts of water per part of 4,4'-oxydiphthalic tetraacid. 1492 parts of the final WC was obtained and it contained 85% of 4,4'-oxydiphthalic tetraacid and less than 30 ppm of hexaethylguanidinium chloride, 464 ppm of chlorophthalic acid and 64 ppm of potassium, with the balance (~5 wt %) being water.

The example illustrates a method of purifying 4,4'-oxydiphthalic anhydride by aqueous hydrolysis and centrifugation.

Example 3

The purpose of Example 3 was also to show that without decantation, a relatively higher level of impurities levels were present in the 4,4' oxydiphthalic anhydride that was produced, as compared to Examples 4 and 5 where decantation is practiced. 2005 parts of a WC of material consisting of 70 wt % 4,4'-oxydiphthalic anhydride, 14 wt % of potassium chloride, 16 wt % of ortho-dichlorobenzene based on total weight of the WC, and some minor impurities as hexaethylguanidinium chloride (1096 ppm) and chlorophthalic anhydride (1637 ppm), was mixed with 437 parts of phosphoric acid (85 wt %) and 12983 parts of water and heated under vacuum until boiling, around 80° C., to form 4,4'-oxydiphthalic tetraacid (ODTA) and chlorophthalic acid (CIDA). The oDCB was removed by azeotrope with water. The weight of the reactor was maintained constant by adding the corresponding amount of water back to the reactor. The process took approximately 34 hours. Subsequently, the mixture was cooled to 22° C. and centrifuged, washing the WC with 10 parts of water per part of 4,4'-oxydiphthalic tetraacid. 1328 parts of the final WC was obtained which contained 86 wt % of 4,4'-oxydiphthalic tetraacid based on total weight of the WC, and less than 30 ppm of hexaethylguanidinium chloride, 724 ppm of chlorophthalic acid, 63 ppm of potassium and the balance (~14 wt %) was water. The substantially pure 4,4'-oxydiphthalic anhydride produced had a sufficiently high purity for use in commercial applications.

Example 4

The purpose of Example 4 was to show that with decantation, a relatively lower level of impurities levels were present in the 4,4'-oxydiphthalic anhydride that was produced, as compared to Examples 2 and 3 where no decantation was practiced. 2667 parts of a WC of material consisting of 65 wt % of 4,4'-oxydiphthalic anhydride, 14 wt % of potassium chloride, 21 wt % of ortho-dichlorobenzene based on total weight of the WC, and some minor impurities as hexaethylguanidinium chloride (1522 ppm) and chlorophthalic anhydride (2450 ppm) was mixed with 437 parts of phosphoric acid (85 wt %) and 10846 parts of water and heated under vacuum until boiling, about 80° C. The oDCB was removed as an azeotrope with water. The weight of the reactor was maintained constant by adding the corresponding amount of water back to the reactor. The process took approximately 36 hours. Subsequently, the mixture was cooled to 24° C. and allowed to settle for 1 hour. The top layer (water with potassium chloride mostly) was removed from the reactor, approximately 8584 parts and the same amount was added back to the reactor vessel as fresh water. After mixing for 30 minutes, the mixture was centrifuged, washing the cake with 10 parts of water per part of 4,4'-oxydiphthalic tetraacid. 1284 parts of the final cake was obtained and it contained 82 wt % of 4,4'-oxydiphthalic tetraacid based on total weight of the final cake, and less than 30 ppm of hexaethylguanidinium chloride, 620 ppm of chloro phthalic acid, and 30 ppm of potassium. The balance (~18%) was water. The substantially pure 4,4'-oxydiphthalic anhydride produced had a sufficiently high purity for use in commercial applications.

The example illustrates that decantation efficiently helps to reduce the final content of potassium in the purified material.

Example 5

The purpose of Example 5 was also to show that with decantation, a relatively lower level of impurities levels were present in the 4,4' oxydiphthalic anhydride that was produced, as compared to Examples 2 and 3 where no decantation was practiced. 2680 parts of a WC of material consisting of 55 wt % of 4,4'-oxydiphthalic anhydride, 14% wt % of potassium chloride, 31 wt % of o-dichlorobenzene based on total weight of the WC, and some minor impurities as hexaethylguanidinium chloride (1672 ppm) and chlorophthalic anhydride (3525 ppm), was mixed with 575 parts of phosphoric acid (85 wt %) and 10795 parts of water and heated under vacuum until boiling, around 80° C. The oDCB was removed from the mixture as an azeotrope with water. The weight of the reactor was maintained constant by adding the corresponding amount of water back to the reactor. The process took approximately 54 hours. Subsequently, the mixture was cooled to 18° C. and allowed to settle for 1 hour. The top layer (water with potassium chloride mostly) was removed from the reactor, approximately 5200 parts, and the same amount of fresh water was added back to the reactor vessel. After mixing for 30 minutes, the mixture was centrifuged, washing the cake with 10 parts of water per part of 4,4'-oxydiphthalic tetraacid made. 1452 parts of the final cake was obtained and it contained 82 wt % of 4,4'-oxydiphthalic tetraacid based on total weight of the final cake, less than 30 ppm of hexaethylguanidinium chloride, 463 ppm of chlorophthalic acid, and 44 ppm of potassium. The balance (~18 wt %) was water.

The results are summarized in Table 2. Decanting and centrifuging significantly lowers the level of potassium impurity relative to the Comparison Examples 2 and 3 which were only centrifuged.

TABLE 2

|  | Decant? (Yes/No) | K (ppm) |
|---|---|---|
| Example 2 | No | 64 |
| Example 3 | No | 63 |

TABLE 2-continued

|  | Decant? (Yes/No) | K (ppm) |
|---|---|---|
| Example 4 | Yes | 30 |
| Example 5 | Yes | 44 |

The results summarized in Table 2 show that decanting reduced potassium levels, as compared to the examples where no decantation occurred.

Example 6

Hydrolysis Wash Liquor Recycle

The purpose Example 6 was show that despite recycle/reuse of the wash liquor in the hydrolysis step of the process, a substantially pure 4,4'-ODPA was produced. The 4,4'-ODPA cake isolated in the DrM that has residual KCl, 4-CIPA and HEGCl was hydrolyzed to 4,4'-oxydiphthalic tetraacid (4,4'-ODTA or ODTA) in the presence of water and phosphoric acid. 4-ClPA is hydrolyzed to its diacid form (4-CIDA) and KCl is dissolved in the water. The resulting 4,4'-ODTA cake is then separated with the centrifuge filter and washed with water to remove residual 4-CIDA, HEGCl and KCl. The desired impurity levels in the 4,4'-ODTA cake are: 4-CIDA less than 1000 ppm, HEGCl less than 30 ppm, and potassium less than 30 ppm. The mother liquor from the filtration is sent to the wastewater for further treatment. The wash liquor (WL) was sent to the WL storage tank and recycled back during the hydrolysis of the next batch. The following example shows that recycling the wash liquor back into the process has no effect on the final 4,4'-ODTA cake purity, thus allowing for significant conservation in water usage. Also, the yield of 4,4'-ODTA is increased because less "new" 4,4'-ODTA is lost to the ML.

4,4'-ODPA cake with different levels of HEGCl and 4-CIPA was used as obtained from the DrM filter. Phosphoric acid (85 wt %) and demineralized water was used as available in the plant.

12000 parts of 4,4'-ODPA cake with the composition listed in Table 5 was added to the reactor. 1200 parts of phosphoric acid and 35800 parts of WL were then charged. The reactor was heated to 100° C. and overhead vapors composed of water and oDCB were condensed and collected in the overhead receiver. The water phase was sent to the waste water system and the oDCB phase was routed to the oDCB recovery system. The reactor weight was maintained constant by adding the WL as makeup water from the WL tank. Reactor was sampled continuously for residual oDCB in the slurry. Once the residual oDCB was less than 200 ppm, the reactor mixture was cooled to less than 40° C. The 4,4'-ODTA slurry was allowed to settle for 2 hrs. The clear liquid on the top was decanted until the final reactor weight was about 18000 parts. Fresh demineralized water was then added to bring the reactor weight back to 43000 parts. The 4,4'-ODTA slurry was then fed in parts (2200 parts per transfer) to the centrifuge filter to isolate the 4,4'-ODTA cake. The ML was sent to the waste water system. The cake was washed with 2200 parts of demineralized water. The WL was sent to the WL tank to be recycled back for the next batch. The cake was then ploughed off the filter and was sampled for impurities. The final product purity is tabulated in Table 3. The results indicate that recycling the WL during hydrolysis does not affect the final product purity.

TABLE 3

| | Composition of ODPA cake used for hydrolysis | | | | | Impurity Level in the final 4,4'-ODTA | | |
|---|---|---|---|---|---|---|---|---|
| Run | 4,4'-ODPA wt % | KCl wt % | oDCB wt % | HEGCl ppm | 4-ClPA ppm | K ppm | 4-ClDA ppm | HEGCl ppm |
| 1 | 38 | 19 | 42 | 3389 | 5143 | 17 | 92 | ND |
| 2 | 35 | 17 | 47 | 6800 | 8700 | 24 | 435 | ND |
| 3 | 34 | 17 | 48 | 2812 | 2714 | 28 | 697 | ND |

Example 7

Filtration to Remove Potassium Salts

The purpose of this Example was to show that potassium levels could be further reduced in the ODPA by conducting a filtration operation after ring closure from the tetraacid. The following provides a method of removing potassium salt contamination from a stream of 4,4'-ODPA solution in oDCB. A high level of potassium in 4,4'-ODPA is detrimental to final polymer quality. 4,4'-ODPA is soluble in oDCB at high temperatures but the potassium species are relatively insoluble. This property was exploited to remove a substantial amount of the residual potassium species by passing the hot solution of 4,4'-ODPA in oDCB through a filter. The effect of filter pore size on the efficiency of potassium salt removal was also studied.

4,4'-ODPA with different potassium impurity levels were obtained from large and small scale experiments. Reagent grade ortho-dichlorobenzene was used as received from Fisher Scientific. Sintered metal filters were obtained from Mott Filtration Corporation.

A 10 wt % solution of ODPA was prepared by heating 10 grams of 4,4'-ODPA in 90 grams of ortho-dichlorobenzene in a 3 neck flask. The mixture was heated to 180° C. under nitrogen. The hot solution was then filtered through a sintered metal filter of either 2 micrometer or 0.5 micrometer pore size. The filtered solution was cooled to room temperature. The 4,4'-ODPA crystallized out of the ortho-dichlorobenzene at room temperature to form a slurry. The 4,4'-ODPA slurry in ortho-dichlorobenzene was then filtered through a 2 Whatman filter paper. The filter cake was then analyzed for potassium species with ICP method (Ion Chromatography/Inductive coupled plasma). The results are shown in Table 4.

TABLE 4

| | Potassium levels (ppm) | |
|---|---|---|
| | Before filtration | After Filtration |
| 2 micrometer filter | 34.2 | 13.6 |
| | 25 | 16.8 |
| | 105 | 58.7 |
| 0.5 micrometer filter | 20.3 | 5.6 |
| | 30.7 | 3.6 |
| | 22.9 | 3.9 |
| | 1280 | 7 |

The potassium levels were measured for the unfiltered and the filtered material using the method described above, except that the filtration study was conducted on a larger scale (approximately 2000 kilogram) and by recycling the impure 4,4'-ODPA solution around a NOMEX® filter multiple times. Table 5 shows the results.

TABLE 5

| Potassium levels (ppm) | |
| --- | --- |
| Before filtration | After Filtration |
| 103 | 4 |

The above data clearly indicate that filtration helps in lowering the potassium levels. Smaller filter size (0.5 micrometer versus 2 micrometer) is more effective in removing the potassium species. These results were further validated using 1 micrometer NOMEX® filters, from Dupont. The cake was formed on the candles during the filtration process, which helped in lowering the effective filter pore size.

Example 8

Example 8 demonstrates how insoluble material from 4,4'-oxydiphthalic anhydride can be removed. The amount of insoluble impurities in ppm in the 4,4'-oxydiphthalic anhydride solution were measured as follows. To a 240 milliliter sample of 4,4'-oxydiphthalic anhydride solution (about 10 wt % solids) was added about 600 milliliter of acetonitrile. The sample was magnetically stirred while heating until a solution was obtained. The weight percent solids X of the solution was determined on a 5 milliliter sample using a Mettler Toledo HR83 Halogen Solid's Analyzer set at 190° C. The total solution weight Y was also recorded. A piece of glass fiber filter paper (Fisher 09-804-70A, 1.5 micrometer) and an aluminum pan were dried using the Mettler Toledo HR83 Halogen Solid's Analyzer set at 190° C. The paper and the pan were cooled for 5 minutes and then weighed to the nearest 0.0001 grams. The filter paper was placed in a Buchner funnel and the warm sample was vacuum filtered. The entire filter paper was washed with about 50 milliliter dimethylformamide (DMF) and 50 milliliter of acetonitrile and finally with 50 milliliter of acetone. The particulates on the filter paper were also washed. After filtration was complete, the filter paper with the insoluble impurities was placed in the pre-dried aluminum pan. The aluminum pan and the filter paper were then dried in the solids analyzer and at 190° C. Once dried, the pan and filter paper were removed and cooled to room temperature. The weight of the cooled aluminum pan and filter paper were then recorded to the nearest 0.000 µg. The difference between the recorded weights of paper and pan before and after the filtration equals the weight of the insoluble impurities Z in grams. The following calculation was used to determine the concentration of the insoluble impurities in ppm, where W is the weight of the solids in grams in the initial solution:

$$W = (X * Y)/100$$

$$\text{ppm insoluble impurities} = 1{,}000{,}000 * Z/W$$

Two trials were run to assess the effectiveness of different types of filters for the removal of insoluble impurities. The goal was to obtain a concentration less than 150 ppm based on the weight of the 4,4'-oxydiphthalic anhydride. Both trials were configured so that the hot 10% solids solution in 1,2-dichlorobenzene at 170° C. to 180° C. was recycled through various types of filters to assess their propensity to remove material and their propensity to 'blind off' and increase the backpressure of the system. Trial #1 evaluated metal filters of various constructions, and insoluble impurities were reduced from 1689 ppm to 108 ppm. Trial #2 evaluated metal filters as well as wound filter media, and insoluble impurities were reduced from 1596 ppm to 147 ppm. The results indicate that insoluble impurities can be reduced in an amount that is more than 0 and less than 150 ppm, based on the 4,4'-oxydiphthalic anhydride. The purified 4,4'-oxydiphthalic anhydride from both trials was of sufficiently high quality that it was used to make polyetherimide having excellent performance characteristics.

While the invention has been described with reference to the embodiments thereof, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. A method for purifying an oxydiphthalic anhydride having structure I, the method comprising steps (a) to (f):

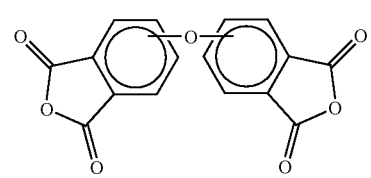

(I)

(a) providing a first mixture comprising at least one oxydiphthalic anhydride, at least one solvent, at least one catalyst, and at least one inorganic salt selected from the group consisting of alkali metal halide salts, alkaline earth metal halide salts, and mixtures thereof, the oxydiphthalic anhydride being present in the first mixture in an amount of 10 to 30 percent by weight based on total weight of the first mixture;

(b) diluting the first mixture with at least one solvent, to provide a second mixture having a solids content of 10 to 30 percent based on total weight of the second mixture;

(c) filtering the second mixture at a temperature below the crystallization point temperature of the oxydiphthalic anhydride and washing the solid with solvent to provide a mother liquor, a wash liquor, and a third mixture of the oxydiphthalic anhydride and salts;

(d) hydrolyzing by adding (1) a water-soluble acid having a $pK_a$ less than or equal to the $pK_a$ of oxydiphthalic tetraacid and (2) water to the third mixture, forming a fourth mixture and heating the fourth mixture; wherein the fourth mixture is cooled to provide a solid-liquid mixture; filtering the solid-liquid mixture to provide a mother liquor and solid component; and washing the solid component with water to provide wash liquor and a fifth mixture of oxydiphthalic tetraacid and water; and (e) ring closing the oxydiphthalic tetraacid by heating the fifth mixture under a temperature and pressure sufficient to convert the oxydiphthalic tetraacid to the oxydiphthalic anhydride, forming a sixth mixture; and (f) filtering the sixth mixture to obtain substantially pure oxydiphthalic anhydride.

2. The method of claim 1, wherein the at least one solvent of step (b) is recycled mother liquor or wash liquor or mixtures thereof from step (c) obtained from a previous batch of first mixture.

3. The method of claim 2, wherein the mother liquor, wash liquor, or mixtures thereof are recycled for a sufficient number of times to achieve a steady state concentration of at least one of chlorophthalic anhydride, catalyst, hydroxyphthalic anhydride, and oxydiphthalic anhydride in the mother liquor or wash liquor.

4. The method of claim 3, wherein the mother liquor or wash liquor or mixtures thereof are recycled 1 to 20,000 times.

5. The method of claim 1, wherein heating the fifth mixture is in the presence of an organic solvent.

6. The method of claim 1, wherein the fifth mixture does not contain an organic solvent.

7. The method of claim 1, wherein the water of step (d) is recycled water selected from the group consisting of mother liquor, wash liquor, and combinations thereof, from step (d) obtained from a previous batch of the fifth mixture.

8. The method of claim 1, wherein the water wash liquor from step (d) is recycled one or more times.

9. The method of claim 1, wherein the water wash liquor from step (d) is recycled from one to 20,000 times.

10. The method of claim 1, wherein the sixth mixture of step (f) comprises less than 100 ppm of an alkali metal ion or alkaline earth metal ion, based on the weight of the oxydiphthalic anhydride present in the sixth mixture.

11. The method of claim 1, wherein the sixth mixture of step (f) comprises less than 2000 ppm chlorophthalic acid, based on the weight of the oxydiphthalic anhydride present in the sixth mixture.

12. The method of claim 1, wherein the third mixture of step (c) comprises less than 2 weight percent chlorophthalic anhydride.

13. The method of claim 1, wherein the sixth mixture of step (e) contains phosphorous in an amount that is less than 100 ppm, based on the weight of the oxydiphthalic anhydride present in the sixth mixture.

14. The method of claim 1, wherein the at least one solvent of step (a) is selected from the group consisting of chlorobenzene, ortho-dichlorobenzene, para-dichlorobenzene, 2,4-dichlorotoluene, 1,2,4-trichlorobenzene, diphenyl sulfone, phenetole, anisole, veratrole, toluene, xylene, mesitylene, and mixtures thereof.

15. The method of claim 1, wherein the at least one solvent of step (a) is ortho-dichlorobenzene.

16. The method of claim 1, wherein the acid of step (d) is phosphoric acid.

17. The method of claim 1, wherein the alkali metal halide is potassium chloride.

18. The method of claim 1, wherein the catalyst of the first mixture is selected from the group consisting of hexaethylguanidinium chloride, hexaethylguanidinium bromide, hexa-n-butylguanidinium bromide, 1,6-bis(N,N',N',N'',N''-penta-n-butylguanidinium)hexane dibromides, 1,6-bis(N-n-butyl-N',N',N'',N''-tetraethylguanidinium)hexane dibromides, phosphonium salts, and combinations thereof.

19. The method of claim 1, wherein the third mixture of step (c) comprises less than 2 weight percent of the catalyst.

20. The method of claim 1, wherein the fifth mixture of step (d) comprises less than 30 ppm of the catalyst.

21. The method of claim 1, wherein filtering in step (c) is by means of a DrM filtration unit, a centrifugal filtration unit, filter press, nutsche, rotary drum filter, or belt filter.

22. The method of claim 1, wherein filtering in step (d), is by means of a DrM filtration unit, a centrifugal filtration unit, filter press, nutsche, rotary drum filter, or belt filter.

23. The method of claim 1, wherein filtering in step (f), is by means of a filtration unit characterized by a filter pore size of 0.5 to 2.0 micrometers.

24. The method of claim 1, wherein the amount of oxydiphthalic tetraacid in the fourth mixture of step (d) ranges from 5 to 30 weight percent based on total weight of the fourth mixture.

25. The method of claim 1, wherein the substantially pure oxydiphthalic anhydride contains less than 30 ppm potassium, less than 1000 ppm chlorophthalic anhydride, and less than 30 ppm catalyst, based on total weight of the oxydiphthalic anhydride in the sixth mixture.

26. A method for purifying 4,4'-oxydiphthalic anhydride having structure (II), the method comprising steps (a) to (f):

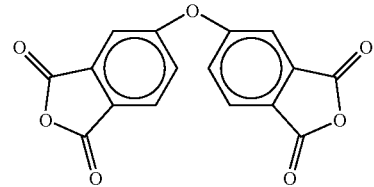

(II)

(a) providing a first mixture comprising 4,4'-oxydiphthalic anhydride, ortho-dichlorobenzene, at least one catalyst including hexaethylguanidinium chloride, and potassium chloride, the 4,4'-oxydiphthalic anhydride being present in the first mixture in an amount of 10 to 30 percent by weight based on total weight of the first mixture;

(b) diluting the first mixture with ortho-dichlorobenzene to provide a second mixture having a solids content of 10 to 30 percent based on total weight of the second mixture;

(c) filtering the second mixture at a temperature of 5° C. to 150° C. and washing the solids with ortho-dichlorobenzene to provide a mother liquor, a wash liquor, and a third mixture of the 4,4'-oxydiphthalic anhydride and potassium chloride;

(d) hydrolyzing by adding phosphoric acid and water to the third mixture, forming a fourth mixture and heating the fourth mixture and subsequently cooling the fourth mixture, wherein a portion of the liquid of the fourth mixture is decanted, rediluted with water, filtered and washed with water to provide wash liquor and a fifth mixture of 4,4'-oxydiphthalic tetraacid and water;

(e) ring closing the oxydiphthalic tetraacid by heating the fifth mixture under a temperature and pressure sufficient to convert the 4,4'-oxydiphthalic tetraacid to the 4,4'-oxydiphthalic anhydride, forming a sixth mixture; and (f) filtering the sixth mixture to obtain substantially pure 4,4'-oxydiphthalic anhydride.

27. The method of claim 1, wherein the substantially pure oxydiphthalic anhydride obtained in step (f) has insoluble impurities in an amount more than 0 and less than 150 ppm relative to the 4,4'-oxydiphthalic anhydride.

28. The method of claim 1, wherein a portion of liquid is decanted from the solid-liquid mixture, and the remaining solid-liquid mixture is rediluted with water before filtering.

* * * * *